(12) United States Patent
Minamino et al.

(10) Patent No.: US 8,986,459 B2
(45) Date of Patent: Mar. 24, 2015

(54) METHOD FOR MANUFACTURING A SUGAR SOLUTION BY ADDING A POLYMER TO THE STARTING SOLUTION BEFORE FILTRATION

(75) Inventors: Atsushi Minamino, Kamakura (JP); Hiroyuki Kurihara, Kamakura (JP); Katsushige Yamada, Kamakura (JP)

(73) Assignee: Toray Industries, Inc. (JP)

( * ) Notice: Subject to any disclaimer, the term of this patent is extended or adjusted under 35 U.S.C. 154(b) by 0 days.

(21) Appl. No.: 14/007,693

(22) PCT Filed: Mar. 28, 2012

(86) PCT No.: PCT/JP2012/058048
§ 371 (c)(1),
(2), (4) Date: Sep. 26, 2013

(87) PCT Pub. No.: WO2012/133477
PCT Pub. Date: Oct. 4, 2012

(65) Prior Publication Data
US 2014/0017729 A1   Jan. 16, 2014

(30) Foreign Application Priority Data
Mar. 29, 2011 (JP) .................................. 2011-071959

(51) Int. Cl.
*C13B 20/16* (2011.01)
*C12P 19/02* (2006.01)
(Continued)

(52) U.S. Cl.
CPC ............. *C13K 13/007* (2013.01); *B01D 61/025* (2013.01); *B01D 61/027* (2013.01); *B01D 61/145* (2013.01); *B01D 61/147* (2013.01); *B01D 61/58* (2013.01); *B01D 2311/04* (2013.01); *B01D 2311/06* (2013.01); *B01D 2311/12* (2013.01); *B01D 2311/2642* (2013.01); *C12N 1/22* (2013.01); *C12P 7/10* (2013.01); *C12P 2203/00* (2013.01); *C13K 1/04* (2013.01); *C13K 13/002* (2013.01); *Y02E 50/16* (2013.01)
USPC ............................................ 127/55; 435/105

(58) Field of Classification Search
USPC ............................................ 127/55; 435/105
See application file for complete search history.

(56) References Cited

U.S. PATENT DOCUMENTS

| | | | |
|---|---|---|---|
| 5,281,279 A | 1/1994 | Gil et al. | |
| 6,184,003 B1 * | 2/2001 | Caboche | ....................... 435/105 |
| 2007/0116828 A1 * | 5/2007 | Prakash et al. | ................. 426/548 |

FOREIGN PATENT DOCUMENTS

| | | |
|---|---|---|
| JP | 62-201606 | 9/1987 |
| JP | 4-305254 | 10/1992 |

(Continued)

OTHER PUBLICATIONS

European Search Report dated Oct. 2, 2014 from corresponding European Application No. 12765172.7.
(Continued)

*Primary Examiner* — Rosanne Kosson
(74) *Attorney, Agent, or Firm* — DLA Piper LLP (US)

(57) ABSTRACT

A method of producing a sugar liquid includes concentrating an aqueous cellulose-derived sugar solution with a nanofiltration membrane and/or reverse osmosis membrane, wherein the concentration is carried out after adding a water-soluble anionic polymer to the aqueous cellulose-derived sugar solution to remove a fermentation inhibitor(s) into a permeate side of the nanofiltration membrane and/or reverse osmosis membrane.

19 Claims, 2 Drawing Sheets

(51) Int. Cl.
*B01D 61/58* (2006.01)
*C12N 1/22* (2006.01)
*C12P 7/10* (2006.01)
*C13K 1/04* (2006.01)
*C13K 13/00* (2006.01)
*B01D 61/02* (2006.01)
*B01D 61/14* (2006.01)

(56) References Cited

FOREIGN PATENT DOCUMENTS

| | | |
|---|---|---|
| JP | 2001-095597 | 4/2001 |
| JP | 2004-187650 | 7/2004 |
| JP | 2005-229821 | 9/2005 |
| JP | 2005-270056 | 10/2005 |
| JP | 2008-161125 | 7/2008 |
| WO | 96/40970 | 12/1996 |
| WO | 2007/097260 | 8/2007 |
| WO | 2008/020444 | 2/2008 |
| WO | 2010/067785 A1 | 6/2010 |

OTHER PUBLICATIONS

Machine translation of JP 2008-535664, Oct. 23, 2013.
Machine translation of JP 2001-511418, Oct. 23, 2013.
Millati, R. et al. "Effect of pH, Time and Temperature of Overliming on Detoxification of Dilute-Acid Hydrolyzates for Fermentation by *Saccaromyces Cerevisiae*," *Process Biochemistry*, 2002, vol. 38, pp. 515-522.
Furuichi, M. et al., "Studies on Enzymic Saccharification, Enzyme Recovery by UF and Sugar Concentration by RO Membranes," *World Congress III of Chemical Engineering*, 1986, pp. 255-257.
Ado, Y., "Alcohol Production from Cellulosic Biomass," *Journal of Wood Science*, 1989, vol. 35, No. 12, pp. 1067-1072 and English translation, Only the English translation was considered.

* cited by examiner

METHOD FOR MANUFACTURING A SUGAR SOLUTION BY ADDING A POLYMER TO THE STARTING SOLUTION BEFORE FILTRATION

TECHNICAL FIELD

The present invention relates to a method for producing a sugar liquid from a cellulose-containing biomass.

BACKGROUND ART

The process of fermentation production of chemical products using sugars as raw materials has been used for producing various industrial materials. At present, as the sugars to be used as fermentation feedstocks, those derived from food materials such as sugar cane, starch and sugar beet are industrially used. However, in view of the fact that rise in the prices of food materials is expected due to future increase in the world population, or in an ethical view of the fact that sugars as industrial materials may compete with sugars for food, a process for efficiently producing a sugar liquid from a renewable nonfood resource, that is, cellulose-containing biomass, or a process for using an obtained sugar liquid as a fermentation feedstock to efficiently convert it to an industrial material, needs to be constructed in the future.

As the prior art for obtaining sugar from biomass, methods wherein concentrated sulfuric acid is used to hydrolyze cellulose and hemicellulose contained in the biomass into monosaccharides represented by glucose and xylose (Patent Documents 1 and 2), and methods wherein pretreatment is carried out for improving the reactivity of biomass, followed by hydrolysis of the biomass by enzymatic reaction (Patent Documents 3 and 4) are generally known.

However, in hydrolysis of a cellulose-containing biomass, decomposition of the cellulose and hemicellulose components and the like proceeds while decomposition reaction of produced sugars such as glucose and xylose proceeds to produce by-products such as furan compounds including furfural and hydroxymethylfurfural, and organic acids including formic acid and acetic acid, which is problematic. These compounds have inhibitory actions during the fermentation step using a microorganism and cause inhibition of the growth of the microorganism, leading to a decreased yield of the fermentation product. Therefore, these compounds are called fermentation inhibitors and have been seriously problematic when a cellulose-containing biomass sugar liquid was used as a fermentation feedstock.

As a method for removing such fermentation inhibitors during the sugar liquid production process, a method called overliming has been disclosed (Non-patent Document 1). In this method, during a step of neutralizing an acid-treated cellulose or saccharified liquid by addition of lime, the mixture is kept for a certain period with heating to about 60° C. to remove fermentation inhibitors such as furfural and HMF together with the gypsum component. However, overliming has only a small effect of removing organic acids such as formic acid, acetic acid and levulinic acid, which is problematic.

Further, as another method for removing fermentation inhibitors, a method wherein water vapor is blown into a sugar liquid prepared from a cellulose-containing biomass to remove fermentation inhibitors by evaporation has been disclosed (Patent Document 5). However, since such a method by evaporative removal is dependent on the boiling points of the fermentation inhibitors, the removal efficiencies for fermentation inhibitors such as organic acids having high boiling points are especially low, so that a large amount of energy is required to achieve sufficient removal efficiencies, which is problematic.

There is also a method wherein fermentation inhibitors are removed by ion exchange (Patent Document 6), but it is problematic in view of the cost. Further, there is a method wherein adsorptive removal is carried out using a wood-based carbide, that is, active carbon or the like, but the subjects to be removed are limited to hydrophobic compounds, which is problematic (Patent Document 7).

Further, there is a method in which fermentation inhibitors are removed with a membrane (Patent Document 8), but the amount of fermentation inhibitors that can be removed into the permeate side is limited, which is problematic.

PRIOR ART DOCUMENTS

Patent Documents

Patent Document 1: Japanese Translated PCT Patent Application Laid-open No. 11-506934
Patent Document 2: JP 2005-229821 A
Patent Document 3: JP 2001-95597 A
Patent Document 4: JP 3041380 B
Patent Document 5: JP 2004-187650 A
Patent Document 6: Japanese Translated PCT Patent Application Laid-open No. 2001-511418
Patent Document 7: JP 2005-270056 A
Patent Document 8: WO 2010/067785

Non-Patent Document

Non-patent Document 1: R Millati et al. "Effect of pH, time and temperature of overliming on detoxification of dilute-acid hydrolyzates for fermentation by *Saccaromyces Cerevisiae*" Process Biochemistry, 38, 515-522 (2002)

SUMMARY OF THE INVENTION

Problems to be Solved by the Invention

Thus, the present invention provides methods for solving the above-mentioned problems, that is, a method wherein fermentation inhibitors produced in the process of producing sugar from a cellulose-containing biomass are removed in the step of producing a sugar liquid, and a method for producing a purified sugar liquid containing only a small mass of fermentation inhibitors.

Means for Solving the Problems

As a result of intensive study of the above problems, the present inventors discovered that, in the process of producing a sugar liquid from a cellulose-containing biomass, a higher effect of removal of fermentation inhibitors from the sugar liquid can be obtained by the operation of adding an anionic polymer to an aqueous solution of sugars derived from the cellulose-containing biomass (hereinafter referred to as aqueous cellulose-derived sugar solution) followed by passing the resulting aqueous sugar solution through a nanofiltration membrane and/or reverse osmosis membrane to remove fermentation inhibitors from the sugar liquid to be used as a fermentation feedstock, compared to the operation of removing fermentation inhibitors from the sugar liquid to be used as a fermentation feedstock by only passing the aqueous cellulose-derived sugar solution through a nanofiltration membrane and/or reverse osmosis membrane. That is, the present invention has the following constitutions.

A method for producing a sugar liquid, the method comprising concentrating an aqueous cellulose-derived sugar solution with a nanofiltration membrane and/or reverse osmosis membrane, wherein the concentration is carried out after adding a water-soluble anionic polymer to the aqueous cellulose-derived sugar solution, to remove a fermentation inhibitor(s) into the permeate side of the nanofiltration membrane and/or reverse osmosis membrane.

A method for producing a chemical product, the method comprising fermentation culture of a microorganism having a capacity to produce a chemical product using, as a fermentation feedstock, a sugar liquid obtained by the production method described above.

Effect of the Invention

By the present invention, organic acids such as acetic acid, formic acid coumaric acid and ferulic acid, which are fermentation inhibitors, can be removed from an aqueous cellulose-derived sugar solution, while sugars such as glucose and xylose can be produced at high purity and high yield. As a result, by using the purified sugar liquid obtained by the present invention as a fermentation feedstock, the efficiencies of fermentation production of various chemical products can be improved.

DETAILED DESCRIPTION OF THE INVENTION

Figure 1:
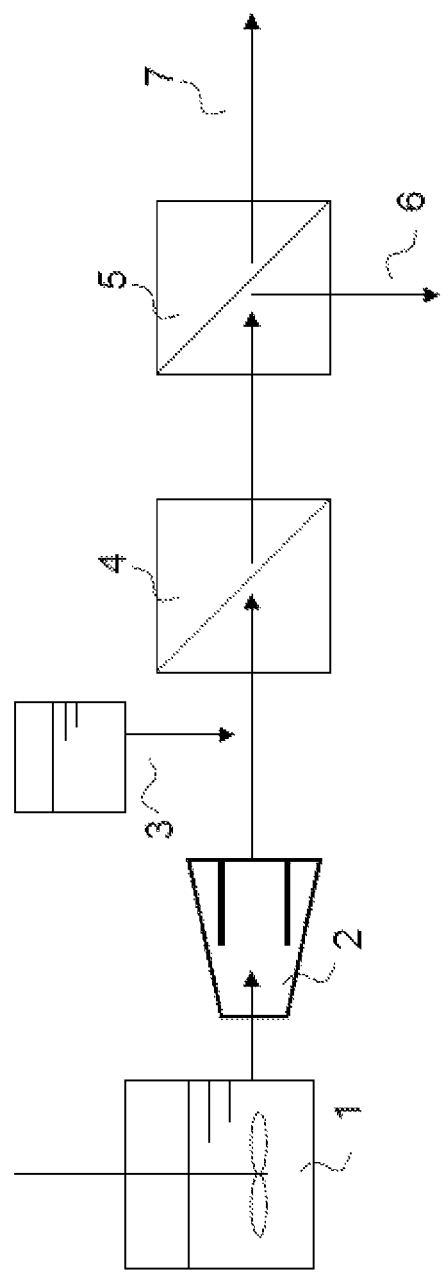
FIG. 1 is a possible example of the method of addition of an anionic polymer in production of a sugar liquid.

Best Mode for Carrying Out the Invention

The present invention is described below more specifically.
The aqueous cellulose-derived sugar solution of the present invention means an aqueous solution containing monosaccharides such as glucose and xylose and oligosaccharides dissolved in water, which solution is prepared by pretreating a cellulose-containing biomass, or by performing enzymatic treatment after the pretreatment, to hydrolyze the cellulose or hemicellulose component in the cellulose-containing biomass.

The cellulose-containing biomass of the present invention means a resource that is derived from an organism and comprises not less than 5% by weight of cellulose. Specific examples of the cellulose-containing biomass include herbaceous biomasses such as bagasse, switchgrass, napier grass, *Erianthus*, corn stover, rice straw and wheat straw; and woody biomasses such as trees and waste building materials. Since such cellulose-containing biomasses contain lignin as aromatic macromolecules in addition to cellulose/hemicellulose, they are also called lignocellulose. By hydrolyzing cellulose and hemicellulose, which are polysaccharide components, contained in the cellulose-containing biomass, a sugar liquid containing monosaccharides that can be utilized as a fermentation feedstock can be obtained.

In the pretreatment of the present invention, a cellulose-containing biomass is subjected to physical or chemical treatment. More specific examples of the pretreatment include, but are not limited to, acid treatment in which treatment is carried out with dilute sulfuric acid, a sulfite or the like at high temperature and high pressure; alkali treatment in which treatment is carried out with an aqueous solution of an alkali such as calcium hydroxide or sodium hydroxide; ammonia treatment in which treatment is carried out with liquid ammonia, ammonia gas or an aqueous ammonia solution; hydrothermal treatment in which treatment is carried out with pressurized hot water; pulverization treatment in which fibers are mechanically cut using a cutter mill, hammer mill, grinder or the like; and steam blasting treatment in which a cellulose-containing biomass is steamed with water vapor for a short time and the pressure is then instantaneously released, to cause pulverization due to volume expansion.

Among the pretreatments, the acid treatment is a treatment method wherein a cellulose-containing biomass is processed with an aqueous acidic solution of sulfuric acid, a sulfite or the like under conditions at high temperature and high pressure, to obtain a pretreated product. In general, in the acid treatment, lignin is dissolved, and the hemicellulose component, which has low crystallinity, is first hydrolyzed, followed by degradation of the cellulose component, which has high crystallinity. Therefore, a liquid containing a larger amount of xylose derived from hemicellulose can be obtained. Further, by setting a plurality of steps, hydrolysis conditions suitable for each of hemicellulose and cellulose can be set, so that the degradation efficiency and the sugar yield can be increased.

The acid to be used in the acid treatment is not limited as long as it causes hydrolysis, and, from the economical viewpoint, sulfuric acid is preferred. The concentration of the acid is preferably 0.1 to 15% by weight, more preferably 0.5 to 5% by weight. The reaction temperature may be set within the range of 100 to 300° C. The reaction time may be set within the range of 1 second to 60 minutes. The number of times of treatment is not limited, and the treatment may be carried out one or more times. The degradation with a saccharifying enzyme after the acid treatment may be carried out for each of the solid matter and the liquid component separated from the pretreated product obtained after the acid treatment, or may be carried out directly with the mixture of the solid matter and the liquid component. Since the solid matter and the liquid component obtained by the acid treatment contain the acid used, neutralization is performed before the hydrolysis reaction with a saccharifying enzyme. It is also possible to use the liquid component alone obtained after the acid treatment. Even without addition of a saccharifying enzyme, the liquid component contains a large amount of monosaccharides and oligosaccharides thereof mainly composed of the hemicellulose-derived component obtained by the hydrolysis with an acid. This liquid component may also be used as the liquid to be applied to a nanofiltration membrane and/or reverse osmosis membrane, without addition of a saccharifying enzyme.

Among the pretreatments, the hydrothermal treatment is a method in which treatment is carried out with pressurized hot water at a temperature of 100 to 400° C. for 1 second to 60 minutes. The treatment is usually carried out such that the cellulose-containing biomass after the treatment, which is insoluble in water at a normal temperature of 25° C., is contained at a concentration of 0.1 to 50% by weight with respect to the total weight of the cellulose-containing biomass and water. The pressure is not limited since it depends on the processing temperature, and is preferably 0.01 to 10 MPa.

The hydrothermal treatment, which is one of the pretreatments, the components eluted into hot water vary depending on the temperature of the pressurized hot water. In general, as the temperature of the pressurized hot water increases, elution of tannin and lignin as the first group from the cellulose-containing biomass occurs first, and elution of hemicellulose as the second group then occurs at a temperature of not less than 140 to 150° C., further followed by elution of cellulose as the third group at a temperature higher than 230° C. Further, at the same time as the elution, hydrolysis of hemicellulose and cellulose may occur. The difference in the eluted components depending on the temperature of the pressurized hot water may be utilized to increase the reaction efficiency of the saccharifying enzyme for cellulose and hemicellulose, by performing a multistage treatment at different temperatures. Here, among the fractions obtained by the hydrothermal treatment, the water-soluble matter containing the components eluted into the pressurized hot water is referred to as the hot-water-soluble matter, and the components other than the hot-water-soluble matter is referred to as the hot-water-insoluble matter.

The hot-water-insoluble matter is a solid matter obtained as a result of elution of large amounts of lignin and the hemicellulose component, and mainly contains di- and higher saccharides as the cellulose (C6) component. In addition to cellulose as the main component, the hot-water-insoluble matter may contain the hemicellulose component and the lignin component. The ratios of contents of these components may vary depending on the temperature of the pressurized hot water during the hydrothermal treatment and on the type of the biomass to be processed. The water content in the hot-water-insoluble matter is 10% to 90%, more preferably 20% to 80%.

The hot-water-soluble matter is a water-soluble matter in the liquid state or slurry state containing hemicellulose, lignin, tannin and a part of the cellulose component eluted into the pressurized hot water in the liquid state or slurry state. The ratio of content of eluted components in the hot-water-soluble matter is usually 0.1% by weight to 10% by weight. Here, the ratio of content of eluted components in the hot-water-soluble matter can be measured using a water content meter (for example, infrared moisture meter FD720, manufactured by Kett Electric Laboratory). More specifically, the ratio may be a value calculated by subtracting the water content of the hot-water-soluble matter obtained using a water content meter from 100%. The eluted components include not only water-soluble components such as monosaccharides and oligosaccharides, but also all other components contained in the water, such as precipitates produced after leaving the hot-water-soluble matter to stand, and colloidal components dispersed, rather than precipitated, in the water.

Since the hot-water-soluble matter contains an especially large amount of fermentation inhibitors, that is, organic acids including formic acid and acetic acid, and furan/aromatic compounds including HMF and furfural, it is usually difficult to perform fermentation production of a chemical product directly using the sugar solution prepared by processing the hot-water-soluble matter with a saccharifying enzyme. Further, the components in the hot-water-soluble matter contain a large amount of colloidal components and particulate components, and these may cause membrane clogging during filtration using a membrane. The liquid component obtained as the hot-water-soluble matter contains a large amount of sugars produced by hydrolysis caused by the hot water, in which not only monosaccharides but also oligosaccharides thereof are contained in a large amount. Further hydrolysis may be carried out by addition of an enzyme, or the liquid component may be used as it is as the liquid to be applied to the nanofiltration membrane and/or reverse osmosis membrane without addition of an enzyme.

Among the pretreatments, the alkali treatment is a treatment method wherein a cellulose-containing biomass is allowed to react in an aqueous alkaline solution which is usually an aqueous solution of a hydroxide salt (other than ammonium hydroxide). By the alkali treatment, lignin, which inhibits the reaction of cellulose/hemicellulose by the saccharifying enzyme, can be removed. As the hydroxide salt, sodium hydroxide or calcium hydroxide is preferably used. The concentration of the alkali in the aqueous solution is preferably within the range of 0.1 to 60% by weight. This solution is added to the cellulose-containing biomass, and the treatment is carried out usually at a temperature within the range of 100 to 200° C., preferably within the range of 110 to 180° C. The number of times of treatment is not limited, and the treatment may be carried out one or more times. In cases where the treatment is carried out 2 or more times, the conditions for the plurality of times of treatment may be different from each other. Since the pretreated product obtained by the alkali treatment contains the alkali, the pretreated product is neutralized before the hydrolysis with a saccharifying enzyme.

Among the pretreatments, the ammonia treatment is a treatment method wherein an aqueous ammonia solution or pure ammonia (in the state of either liquid or gas) is reacted with a cellulose-derived biomass. Examples of the method that may be used include the methods described in JP 2008-161125 A and JP 2008-535664 A. It is said that, in the ammonia treatment, ammonia reacts with the cellulose component to break the crystallinity of cellulose, leading to a remarkable increase in the efficiency of reaction by the saccharifying enzyme. Ammonia is usually added to the cellulose-containing biomass such that the ammonia concentration is within the range of 0.1 to 15% by weight with respect to the cellulose-containing biomass, and the treatment is carried out at 4° C. to 200° C., preferably 60° C. to 150° C. The number of times of treatment is not limited, and the treatment may be carried out one or more times. The pretreated product obtained by the ammonia treatment is subjected to neutralization of ammonia or removal of ammonia before carrying out the hydrolysis reaction with a saccharifying enzyme. The acid reagent to be used for the neutralization is not limited. Examples of the reagent that may be used for the neutralization include hydrochloric acid, nitric acid and sulfuric acid, and, in view of preventing the reagent from acting as a factor causing corrosion of the process piping or as a factor inhibiting fermentation, sulfuric acid is preferred. The removal of ammonia can be carried out by keeping the ammonia-treated product under reduced pressure to evaporate ammonia.

Further, the aqueous cellulose-derived sugar solution may be an aqueous sugar solution obtained by performing the above-described pretreatment and then enzymatic treatment to allow hydrolysis reaction.

In the present invention, the saccharifying enzyme means an enzyme component that has cellulose- or hemicellulose-degrading activity or that aids degradation of cellulose or hemicellulose. Specific examples of the enzyme component include cellobiohydrolase, endoglucanase, exoglucanase, β-glucosidase, xylanase and xylosidase, and biomass-swelling enzymes. Further, the saccharifying enzyme is preferably an enzyme mixture comprising a plurality of types of these components. For example, since hydrolysis of cellulose and hemicellulose can be efficiently carried out by a coordinate effect or complementary effect by such a plurality of enzyme components, an enzyme mixture is preferably used in the present invention.

In the present invention, a saccharifying enzyme produced by a microorganism may be preferably used. For example, the saccharifying enzyme may comprise a plurality of enzyme components produced by a single type of microorganism, or may be a mixture of enzyme components produced by a plurality of types of microorganisms.

The microorganism that produces a saccharifying enzyme is a microorganism that intracellularly or extracellularly produces a saccharifying enzyme, preferably a microorganism that extracellularly produces a saccharifying enzyme. This is because the saccharifying enzyme can be more easily recovered from a microorganism if the microorganism extracellularly produces the saccharifying enzyme.

The microorganism that produces a saccharifying enzyme is not limited as long as the microorganism produces the above-described enzyme component, and the microorganism is preferably a filamentous fungus. A filamentous fungus classified as Trichoderma (hereinafter also referred to as Trichoderma fungus) can be especially preferably used as the microorganism that produces a saccharifying enzyme, since it extracellularly secretes a large amount of various saccharifying enzymes.

The saccharifying enzyme used in the present invention is preferably a saccharifying enzyme derived from a Trichoderma fungus, more preferably a saccharifying enzyme derived from a Trichoderma fungus such as Trichoderma reesei QM9414, Trichoderma reesei QM9123, Trichoderma reesei Rut C-30, Trichoderma reesei PC3-7, Trichoderma reesei CL-847, Trichoderma reesei MCG77, Trichoderma reesei MCG80, Trichoderma viride QM9123 or Trichoderma longibrachiatum (CBS614.94). Further, the saccharifying enzyme may also be derived from a mutant strain prepared from a Trichoderma filamentous fungus by mutagenesis using a mutagen, UV irradiation or the like to enhance the productivity of the saccharifying enzyme. For example, the saccharifying enzyme may be a saccharifying enzyme having a modified composition ratio derived from a mutant strain that was prepared by altering a Trichoderma fungus such that expression of a part of the enzyme component is enhanced.

A commercially available saccharifying enzyme derived from a Trichoderma fungus may also be used. Examples of the commercially available saccharifying enzyme include "Cellic CTec" and "Cellic CTec2", manufactured by Novozymes; "Accellerase 1000", "Accellerase 1500" and "Accellerase DUET", manufactured by Genencor Kyowa; "Cellulase from Trichoderma reesei ATCC 2691", "Cellulase from Trichoderma viride" and "Cellulase from Trichoderma longibrachiatum", manufactured by Sigma Aldrich.

The saccharifying enzyme derived from a Trichoderma fungus can be obtained by culturing the Trichoderma fungus for an arbitrary period in a medium prepared such that production of the enzyme component is possible. The medium component to be used is not limited, and a medium supplemented with cellulose may be preferably used in order to promote production of the saccharifying enzyme. Further, the culture liquid per se, or a culture supernatant obtained by removal of the Trichoderma cells may be preferably used. Further, the medium may be supplemented with an additive(s) such as a protease inhibitor, dispersant, solubilizer and/or stabilizer.

The types of the enzyme components and the ratios of the components in the Trichoderma fungus-derived saccharifying enzyme are not limited. For example, the culture liquid derived from Trichoderma reesei contains cellobiohydrolase, β-glucosidase and the like. In cases of a Trichoderma fungus, highly active cellobiohydrolase is produced into the culture liquid, but, since β-glucosidase is retained in the cell or in the surface layer of the cell, the β-glucosidase activity in the culture liquid is low. Thus, in such cases, β-glucosidase derived from a different species or the same species may be further added to the culture supernatant. As the β-glucosidase derived from a different species to be added in such cases, β-glucosidase derived from Aspergillus is preferably used. Examples of the β-glucosidase derived from Aspergillus include "Novozyme 188", which is commercially available from Novozymes.

The anionic polymer of the present invention means a polymer having a backbone or a side chain moiety charged with a negative ion(s) (anion(s)). The anionic polymer may be in the form of a single anionic monomer, a polymer of a plurality of anionic monomers, or a copolymer comprising anionic monomers. The form of the copolymer is also not limited, and may be any of a random copolymer, block copolymer, graft copolymer and alternating copolymer. Further, the anionic polymer may also be a mixture of 2 or more of polymers, wherein at least one of the polymers is an anionic compound. This is because use of 2 or more types of polymers may increase the effect. Further, the anionic polymer is limited to those soluble in water. The term "soluble in water" means that the solubility of the anionic polymer in water at 25° C. is not less than 1 g/L. The solubility is more preferably not less than 10 g/L. This is because, in cases where the anionic polymer is not soluble in water, clogging of a membrane occurs, and hence the effect of the present invention cannot be exerted. The weight average molecular weight of the anionic polymer is 100 to 20000, more preferably 200 to 10000, in terms of the value measured by the GPC method. Still more preferably, the weight average molecular weight is 300 to 1000 in cases of a phosphate polymer, and 2000 to 8000 in cases of a carboxylate polymer. In cases where the solubility is low or the molecular weight is high, viscosity of the liquid is high, and, in some cases, there is a high possibility of occurrence of fouling of the nanofiltration membrane and/or reverse osmosis membrane due to aggregation of the molecules. Further, the repeat number of basic molecular structure units is preferably within the range of 2 to 200. In cases where the repeat number is not less than 2, the performance of removal of organic acids is high, which is preferred, and in cases where the repeat number is not more than 200, the solubility in water is excellent and hence the possibility of occurrence of aggregation due to interactions among polymer molecules is low, which is preferred.

The anionic polymer of the present invention is preferably a polymer(s) selected from the group consisting of salts of phosphate polymers, phosphate polymers, salts of polycarboxylate polymers, polycarboxylate polymers, and polysulfone polymers. The polymer is more preferably a polymer(s) selected from the group consisting of salts of phosphate polymers, phosphate polymers, salts of polycarboxylate polymers, and polycarboxylate polymers. In particular, polycarboxylate polymers and salts thereof, and inorganic phosphate polymers and salts thereof are preferred. The polymer is still more preferably an inorganic polyphosphate. As the preference increases, the effect to improve the performance of removal of organic acids increases, as described in the Examples. The reason why the performance of removal of organic acids can be obtained in the present invention is not clear, but it is assumed that this is because the counterpart positive ion (cation) retaining an ionized organic acid such as formate ion or acetate ion, for example, sodium ion, potassium ion, calcium ion, silicon ion, magnesium ion, ammonium ion or iron ion likely to be contained in the sugar liquid, is retained by the anionic polymer and permeates through the membrane as a free organic acid molecule. Therefore, the anionic polymer is more preferably a polymer having a property to chelate cations.

The polycarboxylate polymer means a polymer comprising a carboxylate in the backbone or in a side chain moiety. Specific examples of the polycarboxylate polymer include polyacrylic acid, polymethacrylic acid, polymaleic acid, polyfumaric acid, polyitaconic acid, polystyrenecarboxylic acid, poly 1-carboxy-1-methyltetramethylene, poly{1-[(2-carboxyphenyl)iminomethyl]-2-phenylethylene, poly[(E,E)-6-aminohexa-2,4-dienoic acid, poly(22,24-pentacosadiynoic acid), poly(10,12-pentacosadiynoic acid), poly{(1,3-dioxoindoline-5.2 diyl)[bis(trifluoromethyl)methylene](1,3-dioxoindoline-5.2 diyl)(5-carboxy-1,3-phenylene)}, poly(3-carboxyphenylmaleimide), poly(3-methylpyrrol-4-carboxylic acid), poly(2-aminobenzoic acid)poly[dichloro (3-cyanopropyl)methylsilane], poly(2-hydroxy-3-methylbenzeneacetic acid) and poly[1-(carboxyoctyl)ethylene]. The polycarboxylate polymer may be a copolymer of the monomers exemplified above. The polymer may be in the form a salt of an above-described polymer. The polymer is still more preferably polyacrylic acid or polymaleic acid, or a copolymer thereof, or a salt thereof. In cases of a salt, examples of the salt include sodium salt, potassium salt, calcium salt and magnesium salt of each polymer. The salt is more preferably a sodium salt from the economical viewpoint. The polycarboxylate polymer may also be a copolymer with monomers other than monomers comprising a carboxylate. Examples of the polymer include vinyl sulfonic acid, styrene sulfonic acid, acrylonitrile ethylene glycol diolefin hydroxyallyloxypropane sulfonic acid, acrylamide methylpropanesulfonic acid, olefin, isoolefin, vinyl ether, vinyl alcohol, hydroxyethyl methacrylate, acrylamide and vinyl ester. The monomers to be copolymerized other than monomers comprising a carboxylate are preferably monomers comprising a sulfonic acid group, such as vinyl sulfonic acid, styrene sulfonic acid, acrylonitrile ethylene glycol diolefin hydroxyallyloxypropane sulfonic acid and/or acrylamide methylpropanesulfonic acid. The weight average molecular weight of the polycarboxylate polymer is preferably 300 to 10000. Further, the repeat number of basic molecular structure units of the polycarboxylate polymer is preferably 4 to 100. In cases where the polycarboxylate polymer has a weight average molecular weight of not less than 300 and a repeat number of basic molecular structure units of not less than 4, the performance of removal of organic acids is high, which is preferred. Further, in cases where the polycarboxylate polymer has a weight average molecular weight of not more than 10000 and a repeat number of basic molecular structure units of not more than 100, the solubility in water is excellent and the polymer disperses well, so that the membrane performance is not deteriorated, which is preferred.

The phosphate polymer means a polymer having a $PO_3$ moiety, which is a phosphate. The $PO_3$ moiety may be either a functional group or not. Specific examples of the phosphate-containing polymer include inorganic phosphate polymers such as pyrophosphoric acid, acidic pyrophosphate, tripolyphosphoric acid, tetrapolyphosphoric acid, isopolyphosphoric acid, metaphosphoric acid, trimetaphosphoric acid, tetrametaphosphoric acid, hexametaphosphoric acid, acidic hexametaphosphoric acid, isometaphosphoric acid and ultraphosphoric acid, and various sodium salts and potassium salts, as well as Graham's salt, Maddrell's salt and Kurrol's salt. Further examples of the polymer include phosphonic acid and phosphinic acid, and salts thereof, including 2-phosphonobutane tricarboxylic acid-1,2,4-phosphonobutane tricarboxylic acid-1,2,4-1 sodium salt, 2-phosphonobutane tricarboxylic acid-1,2,4-1 potassium salt, 2-phosphonobutane tricarboxylic acid-1,2,4-2 sodium salt, 2-phosphonobutane tricarboxylic acid-1,2,4-2 potassium salt, 2-phosphonobutane tricarboxylic acid-1,2,4-3 sodium salt, 2-phosphonobutane tricarboxylic acid-1,2,4-3 potassium salt, 2-phosphonobutane tricarboxylic acid-1,2,4-4 sodium salt and 2-phosphonobutane tricarboxylic acid-1,2,4-4 potassium salt; 1-hydroxyethylidene-1,1-diphosphonic acid, 1-hydroxyethylidene-1,1-diphosphonic acid-1 sodium salt, 1-hydroxyethylidene-1,1-diphosphonic acid-1 potassium salt, 1-hydroxyethylidene-1,1-diphosphonic acid-2 sodium salt, 1-hydroxyethylidene-1,1-diphosphonic acid-1,2 potassium salt, 1-hydroxyethylidene-1,1-diphosphonic acid-1,3 sodium salt and 1-hydroxyethylidene-1,1-diphosphonic acid-1,3 potassium salt; aminotri(methylenephosphonic acid), aminotri(methylenephosphonic acid)-1 sodium salt, aminotri(methylenephosphonic acid)-1 potassium salt, aminotri(methylenephosphonic acid)-1,2 sodium salt, aminotri(methylenephosphonic acid)-1,2 potassium salt, aminotri(methylenephosphonic acid)-1,3 sodium salt, aminotri(methylenephosphonic acid)-1,3 potassium salt, aminotri(methylenephosphonic acid)-1,4 sodium salt, aminotri(methylenephosphonic acid)-1,4 potassium salt, aminotri(methylenephosphonic acid)-1,5 sodium salt and aminotri(methylenephosphonic acid)-1,5 potassium salt; ethylenediaminetetra(methylenephosphonic acid), ethylenediaminetetra(methylenephosphonic acid)-1 sodium salt, ethylenediaminetetra(methylenephosphonic acid)-1 potassium salt, ethylenediaminetetra(methylenephosphonic acid)-1,2 sodium salt, ethylenediaminetetra(methylenephosphonic acid)-1,2 potassium salt, ethylenediaminetetra(methylenephosphonic acid)-1,3 sodium salt, ethylenediaminetetra(methylenephosphonic acid)-1,3 potassium salt, ethylenediaminetetra(methylenephosphonic acid)-1,4 sodium salt, ethylenediaminetetra(methylenephosphonic acid)-1,4 potassium salt, ethylenediaminetetra(methylenephosphonic acid)-1,5 sodium salt, ethylenediaminetetra(methylenephosphonic acid)-1,5 potassium salt, ethylenediaminetetra(methylenephosphonic acid)-1,6 sodium salt and ethylenediaminetetra (methylenephosphonic acid)-1,6 potassium salt; bis(poly-2-carboxyethyl)phosphinic acid, sodium bis(poly-2-carboxyethyl)phosphinic acid, potassium bis(poly-2-carboxyethyl)phosphinic acid and the like; phytic acid; and phosphate esters of alcohols. The phosphate polymer is more preferably an inorganic polyphosphate. The phosphate polymer preferably has a weight average molecular weight of 160 to 3000. The phosphate polymer preferably has a repeat number of basic molecular structure units of 2 to 20. In cases where the phosphate polymer has a weight average molecular weight of not less than 160 and a repeat number of basic molecular structure units of not less than 2, the performance of removal of organic acids is high, which is preferred. Further, in cases where the phosphate polymer has a weight average molecular weight of not more than 3000 and a repeat number of basic molecular structure units of not more than 20, the solubility in water is excellent and the polymer disperses well, so that the membrane performance is not deteriorated, which is preferred.

The sulfonic acid group polymer means a polymer comprising a sulfonic acid group, and specific examples of the polymer include polystyrene sulfonic acid, acrylonitrile ethylene glycol diolefin hydroxyallyloxypropane sulfonic acid, acrylamidomethyl propane sulfonic acid, 2-acryloylamino-2-methylpropane sulfonic acid, alkylnaphthalene sulfonic acid, metanitrobenzene sulfonic acid, 2-hydroxy-3-allyloxy-1-propane sulfonic acid, isoprenesulfonic acid and 2-acrylamido-2-methylpropanesulfonic acid. The sulfonic acid group polymer preferably has a weight average molecular weight of 600 to 10000. The sulfonic acid group polymer preferably has a repeat number of basic molecular structure units of 4 to 75. In cases where the sulfonic acid group polymer has a weight average molecular weight of not less than 600 and a repeat number of basic molecular structure units of not less than 4, the performance of removal of organic acids is high, which is preferred. Further, in cases where the sulfonic acid group polymer has a weight average molecular weight of not more than 10000 and a repeat number of basic molecular structure units of not more than 75, the solubility in water is excellent and the polymer disperses well, so that the membrane performance is not deteriorated, which is preferred.

The amount of the anionic polymer to be added is not limited, and the amount is preferably 0.005 mg/L to 5000 mg/L, more preferably 0.05 mg/L to 500 mg/L with respect to the volume of the aqueous cellulose-derived sugar solution to be applied to the nanofiltration membrane and/or reverse osmosis membrane. The amount of the anionic polymer to be added is still more preferably 0.5 mg/L to 50 mg/L. This is because addition of a smaller amount of the polymer has only a low effect, while addition of too much amount of the polymer does not lead to remarkable improvement of the effect. The anionic polymer plays a role in chelating anions, especially inorganic anions. The reason why such an anionic polymer having a chelating ability is preferred is as described above.

In the present invention, an acid or alkali may be added together with the anionic polymer. This is because, in some anionic polymers of the present invention, the capacity to remove fermentation inhibitors is enhanced at their optimal pHs. The pH of the aqueous cellulose-derived sugar solution upon addition of the water-soluble anionic polymer is preferably between the pH of the anionic polymer and 12. The pH is more preferably 4 to 9. This is because the optimal pH for the performance of the anionic polymer is within this range, and hence the performance of removal of organic acids as fermentation inhibitors can be increased without decreasing the pH to less than 4 by addition of the anionic polymer. Examples of the acid in the present invention include hydrochloric acid, sulfuric acid, phosphoric acid, nitric acid and organic acids, and the acid is preferably hydrochloric acid, sulfuric acid or phosphoric acid from the economical viewpoint and in consideration of influence on the fermentation step. Examples of the alkali of the present invention include hydroxides such as sodium hydroxide and calcium hydroxide; and amines such as ammonia. The alkali is more preferably sodium hydroxide, calcium hydroxide or ammonia from the economical viewpoint and in consideration of influence on the fermentation step. The adjustment of pH is preferably carried out before addition of the anionic polymer. This is because a part of the anionic polymer in the sugar liquid may be inactivated under the influence of the acid or alkali used for the pH adjustment.

Figure 2:
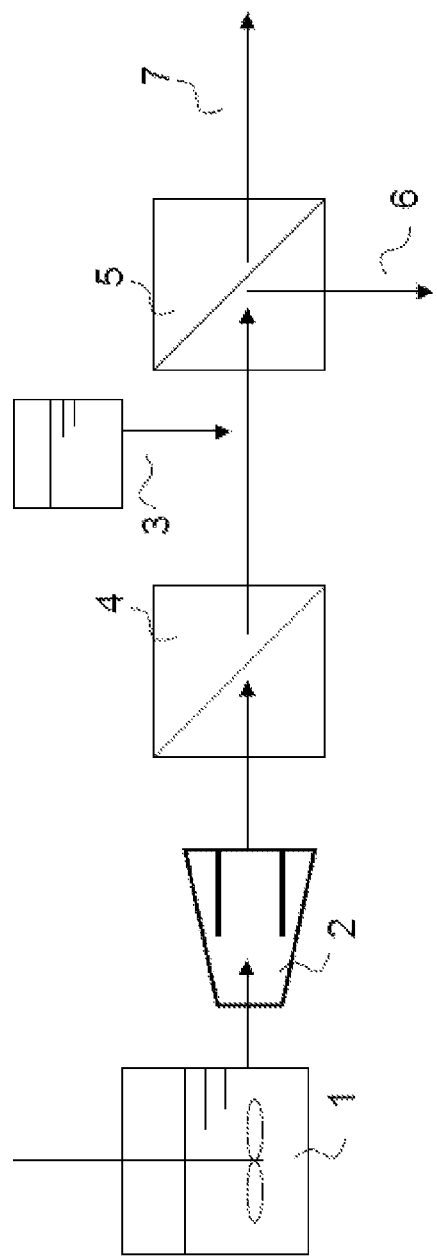
FIG. 2 is a possible example of the method of addition of an anionic polymer in production of a sugar liquid.

In the present invention, the addition of the anionic polymer to the aqueous cellulose-derived sugar solution may be carried out at any stage before the concentration of the aqueous cellulose-derived sugar solution using a nanofiltration membrane and/or reverse osmosis membrane (described later). That is, the addition may be carried out upon the hydrolysis by enzymatic saccharification; upon solid-liquid separation (described later); or upon microfiltration membrane and/or ultrafiltration membrane treatment (described later) that is carried out as a pretreatment for concentration of the aqueous cellulose-derived sugar solution with a nanofiltration membrane and/or reverse osmosis membrane. The treatment is more preferably carried out upon the pre-concentration treatment by the microfiltration membrane and/or ultrafiltration membrane treatment, or at the stage of concentration with a nanofiltration membrane and/or reverse osmosis membrane. This is because loss of the polymer may occur due to the solid-liquid separation or the like by adhesion of the polymer to the solid matter. Still more preferably, as shown in FIG. 2, the anionic polymer is added after the microfiltration membrane and/or ultrafiltration membrane treatment but before the nanofiltration membrane and/or reverse osmosis membrane treatment. This is because, if the timing of addition of the anionic polymer is before the microfiltration membrane and/or ultrafiltration membrane treatment, loss of the anionic polymer may occur due to concentration polarization of the membrane or adhesion of the polymer to the membrane surface, although the anionic polymer does not induce aggregation.

In the present invention, inhibition of fermentation means a phenomenon in which, when a chemical product is produced using as a fermentation feedstock a sugar liquid that was prepared using a cellulose-containing biomass as a raw material, the amount of the chemical product produced or accumulated, or the production rate of the chemical product, decreases due to fermentation inhibitors, as compared to a case where a reagent monosaccharide is used as a fermentation feedstock. The extent of such fermentation inhibition varies depending on the types and amounts of the fermentation inhibitors present in the sugar liquid, and also varies depending on the species of the microorganism employed and the type of the chemical product to be produced thereby. The aqueous cellulose-derived sugar solution of the present invention contains fermentation inhibitors in any case, although their components and contents vary depending on the conditions for the pretreatment and the saccharification reaction, the type of the cellulose-containing biomass, and the like. Therefore, by subjecting the aqueous cellulose-derived sugar solution to the treatment with a nanofiltration membrane and/or reverse osmosis membrane after addition of the anionic polymer, fermentation inhibitors can be efficiently removed.

The fermentation inhibitors are substances produced by the step of pretreatment of a cellulose-containing biomass and the step of hydrolysis by a saccharifying enzyme, which substances inhibit, as described above, fermentation in the step of fermentation using as a raw material the sugar liquid obtained by the production method of the present invention. The fermentation inhibitors are roughly classified into organic acids, furan compounds and phenolic compounds.

Specific examples of the organic acids include acetic acid, formic acid and malic acid. Specific examples of the furan compounds include furfural and hydroxymethylfurfural (HMF). These organic acids and furan compounds are products produced by decomposition of glucose or xylose, which are monosaccharides. Specific examples of the phenolic compounds include vanillin, acetovanillin, coumaric acid, ferulic acid, vanillic acid, syringic acid, gallic acid, coniferyl aldehyde, dihydroconiferyl alcohol, hydroquinone, catechol, acetoguaicone, homovanillic acid, 4-hydroxybenzoic acid, and 4-hydroxy-3-methoxyphenyl derivatives (Hibbert's ketones). These phenolic compounds are derived from lignin or lignin precursors.

In cases where a waste building material, plywood or the like is used as the cellulose-containing biomass, components such as adhesives and paints used in the lumbering process may be contained as fermentation inhibitors. Examples of the adhesives include urea resins, melamine resins, phenol resins, and urea/melamine copolymers. Examples of fermentation inhibitors derived from such adhesives include acetic acid, formic acid and formaldehyde.

In particular, as described in the Examples below, addition of an anionic polymer increases permeability of the nanofiltration membrane and/or reverse osmosis membrane to organic acids, furan compounds comprising a carboxyl group, and phenolic compounds comprising a carboxyl group. Thus, removal of organic acids from the aqueous cellulose-derived sugar solution can be efficiently carried out.

Examples of the furan compounds comprising a carboxyl group include furancarboxylic acid and benzofuran-2-carboxylic acid. Examples of the phenolic compounds comprising a carboxyl group include coumaric acid, ferulic acid, vanillic acid, syringic acid, gallic acid, homovanillic acid and 4-hydroxybenzoic acid.

The aqueous cellulose-derived sugar solution contains at least one of the substances as a fermentation inhibitor(s), and the solution usually contains a plurality of the substances. These fermentation inhibitors can be detected and quantified by a common analytical method such as thin layer chromatography, gas chromatography or high performance liquid chromatography.

The nanofiltration membrane used in the present invention is also called a nanofilter (nanofiltration membrane, NF membrane), and generally defined as a "membrane that allows permeation of monovalent ions, but blocks divalent ions". The membrane is considered to have fine voids having sizes of about several nanometers, and mainly used to block fine particles, molecules, ions and salts in water.

The reverse osmosis membrane used in the present invention is also called an RO membrane, and generally defined as a "membrane having a desalination function that can also remove monovalent ions". The membrane is considered to have ultrafine voids having sizes ranging from about several angstroms to several nanometers, and mainly used for removal of ionic components, such as seawater desalination and production of ultrapure water The aqueous cellulose-derived sugar solution is filtered through one or both of a nanofiltration membrane and reverse osmosis membrane, to obtain a purified sugar liquid as the membrane non-permeate fraction. Sugars dissolved in the aqueous cellulose-derived sugar solution, especially monosaccharides such as glucose and xylose, can be blocked or separated into the feed side, while fermentation inhibitors can be removed by allowing them to permeate as the membrane permeate fraction (filtrate).

The performance of the nanofiltration membrane or reverse osmosis membrane used in the present invention can be evaluated by calculating the permeation rate (%) of the subject compound (fermentation inhibitor, monosaccharide or the like) contained in the sugar solution. The method for calculating the permeation rate (%) is shown in Equation 1.

Permeation rate (%)=(concentration of subject compound in permeate side/concentration of subject compound in feed side)×100 (Equation 1)

The method for measuring the concentration of the subject compound in Equation 1 is not restricted as long as the method allows accurate and reproducible measurement, and examples of the method that may be preferably used include high performance liquid chromatography and gas chromatography. In both nanofiltration membrane and reverse osmosis membrane used in the present invention, the permeation rates of monosaccharides are preferably low, and the permeation rates of fermentation inhibitors are preferably high.

A nanofiltration membrane generally has a larger pore size than a reverse osmosis membrane. Therefore, it is considered that, in cases where a nanofiltration membrane is used, the amount of fermentation inhibitors removed by permeation through the membrane is relatively large, while the amount of monosaccharides as the products of interest lost into the permeate side is also relatively large, as compared to cases where a reverse osmosis membrane is used. In particular, in cases where the sugar concentration is high, this tendency strongly appears. Conversely, in cases where a reverse osmosis membrane is used, the amount of high-molecular-weight fermentation inhibitors removed is considered to be smaller since a reverse osmosis membrane has a smaller pore size than a nanofiltration membrane. Therefore, it is preferred to select an appropriate membrane(s) among nanofiltration membranes and reverse osmosis membranes in consideration of the contents and the molecular weights of the major fermentation inhibitors in the aqueous cellulose-derived sugar solution. A plurality of types of membranes may be selected among nanofiltration membranes and reverse osmosis membranes depending on the composition of the sugar solution, and may be used in combination.

When a nanofiltration membrane is used, as the concentration of monosaccharides captured in the feed side (concentrate side) of the nanofiltration membrane increases, the rate of loss of monosaccharides into the permeate side (filtrate side) sharply increases in some cases. On the other hand, when a reverse osmosis membrane is used, loss of monosaccharides hardly occurs even at an increased monosaccharide concentration in the membrane non-permeate side. However, in view of removal of fermentation inhibitors, a nanofiltration membrane has higher performance than a reverse osmosis membrane. Therefore, in cases where a nanofiltration membrane and reverse osmosis membrane are used in combination, it is preferred to remove fermentation inhibitors using a nanofiltration membrane to a concentration at which loss of sugars into the membrane permeate side can be judged to be small, followed by use of a reverse osmosis membrane that allows concentration of monosaccharides without loss.

Examples of the nanofiltration membrane which may be used in the present invention include membranes composed of macromolecular materials such as cellulose acetate polymers; polyamide; polyester; polyimide; vinyl polymers including polyvinyl alcohol; polysulfone; sulfonated polysulfone; polyethersulfone; and sulfonated polyethersulfone. The membrane may also be a membrane comprising a plurality of these materials. In terms of the membrane structure, the membrane may be either an asymmetric membrane, which has a dense layer on at least one side and micropores having pore sizes that gradually increase in the direction from the dense layer toward the inside of the membrane or the other side of the membrane, or a composite membrane, which has a very thin functional layer formed by another material on the dense layer of an asymmetric membrane. Examples of the composite membrane which may be used include the composite membrane described in JP 62-201606 A, which has a nanofilter composed of a polyamide functional layer on a support membrane comprising polysulfone as a membrane material.

Among these nanofiltration membranes, a composite membrane having a functional layer composed of a polyamide is preferred since it has high pressure resistance, high permeability and high solute-removal performance, which make the membrane highly potential. For maintenance of durability against operating pressure, and of high permeability and high blocking performance, the membrane preferably has a structure in which a polyamide is used as a functional layer and the layer is retained by a support composed of a porous membrane or a non-woven fabric. Further, as the polyamide semipermeable membrane, a composite semipermeable membrane having, on a support, a functional layer of a cross-linked polyamide obtained by polycondensation reaction between a polyfunctional amine and a polyfunctional acid halide is suitable.

In the nanofiltration membrane having a polyamide functional layer, preferred examples of the carboxylic acid component of the monomers constituting the polyamide include aromatic carboxylic acids such as trimesic acid, benzophenone tetracarboxylic acid, trimellitic acid, pyromellitic acid, isophthalic acid, terephthalic acid, naphthalene dicarboxylic acid, diphenylcarboxylic acid and pyridinecarboxylic acid. In view of solubility to film-forming solvents, trimesic acid, isophthalic acid and terephthalic acid, and mixtures thereof are more preferred.

Preferred examples of the amine component of the monomers constituting the polyamide include primary diamines having an aromatic ring, such as m-phenylenediamine, p-phenylenediamine, benzidine, methylene bis dianiline, 4,4'-diaminobiphenylether, dianisidine, 3,3',4-triaminobiphenylether, 3,3',4,4'-tetraminobiphenylether, 3,3'-dioxybenzidine, 1,8-naphthalenediamine, m(p)-monomethylphenylenediamine, 3,3'-monomethylamino-4,4'-diaminobiphenylether, 4,N,N'-(4-aminobenzoyl)-p(m)-phenylenediamine-2,2'-bis(4-aminophenylbenzoimidazole), 2,2'-bis(4-aminophenylbenzooxazole) and 2,2'-bis(4-aminophenylbenzothiazole); and secondary diamines such as piperazine, piperidine and derivatives thereof. A nanofiltration membrane having a functional layer composed of a cross-linked polyamide comprising, among these, piperazine or piperidine as monomers is preferably used since it has heat resistance and chemical resistance in addition to pressure resistance and durability.

The polyamide more preferably contains as a major component the cross-linked piperazine polyamide or cross-linked piperidine polyamide and further contains a constituting component represented by Chemical Formula (1). The polyamide still more preferably contains a cross-linked piperazine polyamide as a major component and further contains a constituting component represented by Chemical Formula (1). Further, especially preferably, in Chemical Formula 1, n=3. Examples of the nanofiltration membrane having a functional layer composed of a polyamide containing a cross-linked piperazine polyamide as a major component and further containing a constituting component represented by Chemical Formula (1) include the one described in JP 62-201606 A, and specific examples of the membrane include UTC60, manufactured by Toray Industries, Inc., which is a cross-linked piperazine polyamide nanofiltration membrane having a functional layer composed of a polyamide containing a cross-linked piperazine polyamide as a major component and further containing a constituting component represented by Chemical Formula (1) wherein n=3.

[Chemical Formula 1]

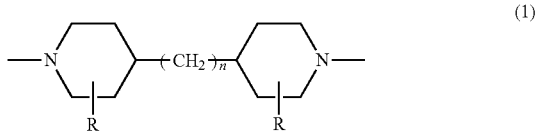

(1)

In Chemical Formula 1, R represents —H or —CH$_3$, and n represents an integer of 0 to 3.

A nanofiltration membrane is generally used as a spiral-wound membrane element, and the nanofiltration membrane used in the present invention is also preferably used as a spiral-wound membrane element. Specific preferred examples of the nanofiltration membrane module include GEsepa DK series, HL series and DL series, which are cellulose acetate nanofiltration membranes manufactured by GE Osmonics; NTR-7410 and NTR-7450, which have sulfonated polysulfone functional membranes; NTR-725HF, NTR-7250, NTR-729HF, NTR-769SR and NTR-759HR, manufactured by Nitto Denko Corporation, having a functional membrane composed of polyvinyl alcohol manufactured by Nitto Denko Corporation; NF99, NF99HF and NF97, which are nanofiltration membranes manufactured by Alfa-Laval having a polyamide functional layer; NF-45, NF-90, NF-200, NF-270 and NF-400, which are nanofiltration membranes having a functional layer composed of a cross-linked piperazine polyamide, manufactured by Filmtec Corporation; and SU-210, SU-220, SU-600 and SU-610, which are nanofiltration membrane modules manufactured by Toray Industries, Inc., having a functional layer composed of a polyamide containing a cross-linked piperazine polyamide as a major component. The nanofiltration membrane element is more preferably NF99 or NF99HF, which are nanofiltration membranes having a functional layer composed of a polyamide, manufactured by Alfa-Laval; NF-45, NF-90, NF-200 or NF-400, which are nanofiltration membranes having a functional layer composed of a cross-linked piperazine polyamide, manufactured by Filmtec Corporation; or SU-210, SU-220, SU-610 or SU-620, which are nanofiltration membrane modules manufactured by Toray Industries, Inc., having a functional layer composed of a polyamide containing a cross-linked piperazine polyamide as a major component. The nanofiltration membrane element is still more preferably SU-210, SU-220, SU-610 or SU-620, which are nanofiltration membrane modules manufactured by Toray Industries, Inc., having a functional layer composed of a polyamide containing a cross-linked piperazine polyamide as a major component.

In the filtration through a nanofiltration membrane, the aqueous cellulose-derived sugar solution is preferably fed to the nanofiltration membrane at a pressure within the range of 0.1 MPa to 8 MPa, although a preferred pressure varies depending on the concentration of the solution. In cases where the pressure is less than 0.1 MPa, the membrane permeation rate may be low, while in cases where the pressure is more than 8 MPa, the membrane may be damaged. In cases where the pressure is 0.5 MPa to 6 MPa, the membrane permeation flux is high, so that the sugar solution can be efficiently allowed to permeate, which is especially preferred.

In terms of the material of the reverse osmosis membrane used in the present invention, examples of the membrane include a composite membrane having a functional layer composed of a cellulose acetate polymer (hereinafter also referred to as a cellulose acetate reverse osmosis membrane) and a composite membrane having a functional layer composed of a polyamide (hereinafter also referred to as a polyamide reverse osmosis membrane). Here, examples of the cellulose acetate polymer include polymers prepared with organic acid esters of cellulose such as cellulose acetate, cellulose diacetate, cellulose triacetate, cellulose propionate and cellulose butyrate, which may be used individually, as a mixture, or as a mixed ester. Examples of the polyamide include linear polymers and cross-linked polymers comprising aliphatic and/or aromatic diamine monomers.

Specific examples of the reverse osmosis membrane used in the present invention include polyamide reverse osmosis membrane modules manufactured by Toray Industries, Inc., such as ultralow-pressure type modules SUL-G10 and SUL-G20, low-pressure type modules SU-710, SU-720, SU-720F, SU-710L, SU-720L, SU-720LF, SU-720R, SU-710P, SU-720P, TMG10, TMG20-370 and TMG20-400, as well as high-pressure type modules SU-810, SU-820, SU-820L and SU-820FA; cellulose acetate reverse osmosis membranes manufactured by the same manufacturer SC-L100R, SC-L200R, SC-1100, SC-1200, SC-2100, SC-2200, SC-3100, SC-3200, SC-8100 and SC-8200; NTR-759HR, NTR-729HF, NTR-70SWC, ES10-D, ES20-D, ES20-U, ES15-D, ES15-U and LF10-D, manufactured by Nitto Denko Corporation; RO98pHt, R099, HR98PP and CE4040C-30D, manufactured by Alfa-Laval; GE Sepa AG series and AK series, manufactured by GE; BW30-4040, TW30-4040, XLE-4040, LP-4040, LE-4040, SW30-4040 and SW30HRLE-4040, manufactured by FilmTec Corporation; TFC-HR and TFC-ULP, manufactured by KOCH; and ACM-1, ACM-2 and ACM-4, manufactured by TRISEP.

In the present invention, a reverse osmosis membrane containing a polyamide material is preferably used. This is because, in cases where a cellulose acetate membrane is used for a long time, enzymes used in the pretreatment step, especially a part of the cellulase component, may permeate through the membrane to cause degradation of cellulose as the membrane material.

Examples of the form of the reverse osmosis membrane appropriately used in the present invention include a flat membrane, spiral-wound membrane and hollow fiber membrane.

In a reverse osmosis membrane having a polyamide functional layer, preferred examples of the carboxylic acid component and the amine component of the monomers constituting the polyamide are the same as those for the nanofiltration membrane described above having a polyamide functional layer.

In the filtration through a reverse osmosis membrane, the aqueous cellulose-derived sugar solution is preferably fed to the reverse osmosis membrane at a pressure within the range of 0.5 MPa to 8 MPa, although a preferred pressure varies depending on the concentration of the solution. In cases where the pressure is less than 0.5 MPa, the membrane permeation rate may be low, while in cases where the pressure is more than 8 MPa, the membrane may be damaged. In cases where the filtration pressure is 1 MPa to 7 MPa, the membrane permeation flux is high, so that the sugar solution can be efficiently allowed to permeate and the possibility of damaging the membrane is small, which is more preferred.

In the present invention, fermentation inhibitors are removed from the sugar solution by addition of a water-soluble anionic macromolecule to the solution and the subsequent permeation of the fermentation inhibitors through a nanofiltration membrane and/or reverse osmosis membrane. Among fermentation inhibitors, organic acids, furan compounds comprising a carboxyl group, and phenolic compounds comprising a carboxyl group can be preferably allowed to permeate, and removed. On the other hand, sugars contained in the sugar solution are blocked or separated into the feed side of the nanofiltration membrane and/or reverse osmosis membrane.

The aqueous cellulose-derived sugar solution in the present invention is preferably filtered through a microfiltration membrane and/or ultrafiltration membrane prior to the treatment with a nanofiltration membrane and/or reverse osmosis membrane. This is because, by the filtration through a microfiltration membrane and/or ultrafiltration membrane, fouling of the nanofiltration membrane and/or reverse osmosis membrane can be prevented.

The microfiltration membrane in the present invention is a membrane whose functional surface has an average pore size of not more than 1 μm. The microfiltration membrane more preferably has a porous functional surface. The porous microfiltration membrane means a membrane whose functional surface has a three-dimensional network structure in which voids are formed such that they communicate with each other. The membrane is more preferably a porous microfiltration membrane having an average pore size of not more than 0.25 μm.

As the average pore size of the microfiltration membrane, the nominal pore size presented by each separation membrane manufacturer may be employed, or the average pore size may be actually measured. As the method for measuring the pore size of the microfiltration membrane, the direct observation method may be applied. In the direct observation method, a scanning electron microscope (SEM) is used to observe the surface pores present inside an area of 10 μm×9 μm on the surface of the microfiltration membrane, and the diameters of the pores are measured. By calculating their average value, the average pore size can be determined. Further, in cases of a membrane whose pore size cannot be determined by the direct observation method, such as a nonwoven fabric or woven fabric, a bubble point test is carried out to determine the pore size. In the bubble point method, an air pressure is applied from the secondary side of the membrane, and the minimum pressure at which generation of an air bubble can be observed on the membrane surface is measured. According to a relational expression between the surface tension of the liquid used and the pressure, the average pore size can be calculated. More specifically, the measurement can be carried out according to ASTM F316-03 (bubble point method) using, for example, a penetrating-pore size distribution/gas permeability analyzer manufactured by Bel Japan, Inc.

Examples of the material of the microfiltration membrane used in the present invention include cellulose series, aromatic polyamide, polyvinyl alcohol, polysulfone, polyethersulfone, polyvinylidene fluoride, polyethylene, polyacrylonitrile, polypropylene, polycarbonate, polytetrafluoroethylene, ceramics and metals. Preferred among these are aromatic polyamide, polyvinyl alcohol, polysulfone, polyvinylidene fluoride, polyethylene, polyacrylonitrile, polypropylene, polycarbonate and polytetrafluoroethylene since these are not influenced by saccharifying enzymes contained in the enzymatically saccharified liquid and have excellent ability to remove the insoluble solid matter.

The ultrafiltration membrane in the present invention is a membrane usually having a molecular weight cutoff of 1000 to 100000, and referred to as an ultrafiltration, UF membrane or the like for short. Since the pore size of an ultrafiltration membrane is too small, it is difficult to measure the pore size of its membrane surface under the electron microscope. Therefore, a value called the molecular weight cutoff is used as an index of the pore size instead of the average pore size. As is described, for example, that "The curve obtained by plotting the molecular weight of the solute along the abscissa and the blocking rate along the ordinate is called the molecular weight cutoff curve. The molecular weight with which the blocking rate reaches 90% is called the molecular weight cutoff of the membrane." (The Membrane Society of Japan ed., "Membrane Experiment Series, Vol. III, Artificial Membrane, editorial committee members: Shoji Kimura, Shin-ichi Nakao, Haruhiko Ohya and Tsutomu Nakagawa (1993, Kyoritsu Shuppan Co., Ltd.), p. 92), the molecular weight cutoff is well known to those skilled in the art as an index representing the membrane performance of an ultrafiltration membrane.

In the method for producing a sugar liquid of the present invention, an ultrafiltration membrane having a molecular weight cutoff within the range of 500 to 40000 is more preferably used since it allows efficient recovery of the saccharifying enzyme used for enzymatic saccharification. This is because the saccharifying enzyme is a mixture of a plurality of types of components, and, among the saccharifying enzymes in the mixture, those having smaller molecular weights have molecular weights of about 40000. The form of the ultrafiltration membrane to be used is not limited, and the membrane may be any of a spiral-wound membrane, hollow fiber membrane, tubular membrane and flat membrane. By reusing the recovered saccharifying enzyme in the hydrolysis reaction, the amount of enzyme used can be reduced.

Examples of the material of the ultrafiltration membrane include, but are not limited to, organic materials such as cellulose, cellulose ester, polysulfone, sulfonated polysulfone, polyethersulfone, sulfonated polyethersulfone, chlorinated polyethylene, polypropylene, polyolefin, polyvinyl alcohol, polymethyl methacrylate, polyvinylidene fluoride and polytetrafluoroethylene; metals such as stainless steel; and inorganic materials such as ceramics. The material of the ultrafiltration membrane may be appropriately selected in consideration of properties of the hydrolysate and the running cost, and is preferably an organic material, more preferably chlorinated polyethylene, polypropylene, polyvinylidene fluoride, polysulfone or polyethersulfone. Specific examples of the material include Type G-5, Type G-10, Type G-20, Type G-50, Type PW and Type HWS UF, manufactured by DESAL; HFM-180, HFM-183, HFM-251, HFM-300, HFM-116, HFM-183, HFM-300, HFK-131, HFK-328, MPT-U20, MPS-U20P and MPS-U20S, manufactured by KOCH; SPE1, SPE3, SPE5, SPE10, SPE30, SPV5, SPV50 and SOW30, manufactured by Synder; products of Microza (registered trademark) UF series, manufactured by Asahi Kasei Corporation, having molecular weight cutoffs of 3000 to 100000; and NTR7410, manufactured by Nitto Denko Corporation.

The filtration through a microfiltration membrane and/or ultrafiltration membrane in the present invention may be either cross-flow filtration or dead-end filtration. In view of energy consumption by the pump, dead-end filtration is preferred. However, a liquid with bad filterability is preferably subjected to cross-flow filtration. Further, a process such as back washing or aeration is preferably carried out during the filtration. This is because fouling of the membrane is suppressed thereby. After the filtration through a microfiltration membrane, the obtained permeate is passed through an ultrafiltration membrane to remove the saccharifying enzyme as the non-permeate fraction, and the permeate fraction is subjected to a filtration process through a nanofiltration membrane and/or reverse osmosis membrane. Here, from the economical viewpoint, the removed saccharifying enzyme may be reused in the enzymatic saccharification process.

Before the filtration through a microfiltration membrane and/or ultrafiltration membrane, solid-liquid separation treatment may be carried out as a pretreatment for suppression of fouling substances. The method of solid-liquid separation is not restricted. According to "Food Engineering Basic Course, Solid-liquid Separation" (Korin Publishing Co., Ltd.), specific examples of the method of solid-liquid separation include the centrifugation method, compression separation method, filtration method, flotation separation method and precipitation separation method. Examples of the centrifugation method include methods using a horizontal continuous centrifuge (screw decanter treatment), disk centrifuge (De Laval treatment), centrifugal filter or Sharples ultracentrifuge; examples of the filtration method include methods using a belt filter, belt press, screw press, precoat filter or filter press; examples of the flotation separation method include methods using a continuous flotation separation apparatus; and examples of the precipitation separation method include methods using an aggregation precipitation apparatus or rapid precipitation apparatus; but the method is not limited to any of these. However, any one of these, or a combination of two or more of these, enables reduction in the load on the membrane during the microfiltration membrane and/or ultrafiltration membrane treatment.

After the removal of fermentation inhibitors by the above-described method and the concentration using a nanofiltration membrane and/or reverse osmosis membrane, the sugar liquid is preferably further filtered through an ultrafiltration membrane having a molecular weight cutoff of 500 to 2000. In cases where the anionic polymer of the present invention is a substance that deteriorates the fermentation performance, the ultrafiltration membrane may be used to obtain a sugar liquid as a filtrate from which the anionic polymer has been removed or reduced. This can increase the fermentation efficiency in the later step. Further, the anionic polymer recovered from the feed side of the ultrafiltration membrane can be reused to reduce the amount of the anionic polymer used.

By performing fermentation culture of a microorganism having an ability to produce a chemical product using as a fermentation feedstock a purified sugar liquid obtained by the present invention, the chemical product can be produced. The purified sugar liquid obtained by the present invention contains, as a major component(s), glucose and/or xylose, which are carbon sources for the growth of microorganisms or cultured cells. On the other hand, the contents of fermentation inhibitors such as furan compounds, organic acids and aromatic compounds are very small. Therefore, the purified sugar liquid can be effectively used as a fermentation feedstock, especially as a carbon source.

In the present invention, examples the microorganism or cultured cells used in the method of for producing a chemical product include yeasts such as baker's yeast; bacteria such as *E. coli* and coryneform bacteria; filamentous fungi; actinomycetes; animal cells; and insect cells; which are commonly used in the fermentation industry. The microorganism or cultured cells to be used may be isolated from a natural environment, or may be prepared by partial modification of properties of a microorganism or cells by mutation or gene recombination. In particular, since a sugar liquid derived from a cellulose-containing biomass contains pentoses such as xylose, a microorganism having enhanced metabolic pathways for pentoses may be preferably used.

In the present invention, the medium used in the method for producing a chemical product is preferably a liquid medium containing, in addition to the purified sugar liquid, nitrogen sources, inorganic salts, and, as required, organic micronutrients such as amino acids and vitamins. The purified sugar liquid of the present invention contains as carbon sources monosaccharides which can be used by microorganisms, such as glucose and xylose, but, in some cases, sugars such as glucose, sucrose, fructose, galactose and lactose; saccharified starch liquids containing these sugars; sweet potato molasses; sugar beet molasses; high test molasses; organic acids such as acetic acid; alcohols such as ethanol; glycerin; and the like may be further added thereto as carbon sources, to provide a fermentation feedstock. Examples of the nitrogen sources that may be used include ammonia gas, aqueous ammonia, ammonium salts, urea and nitric acid salts; and other organic nitrogen sources used supplementarily such as oilcakes, soybean-hydrolyzed liquids, casein digests, other amino acids, vitamins, corn steep liquors, yeasts or yeast extracts, meat extracts, peptides such as peptones, and cells of various fermentation microorganisms and hydrolysates thereof. Examples of the inorganic salts which may be added as appropriate include phosphoric acid salts, magnesium salts, calcium salts, iron salts and manganese salts.

In cases where the microorganism used in the present invention requires a specific nutrient for its growth, the nutrient may be added as a preparation or natural product containing it. An anti-forming agent may also be added as required.

The microorganism is usually cultured at a pH within the range of 4 to 8, at a temperature within the range of 20 to 40° C. The pH of the culture medium is adjusted in advance with an inorganic or organic acid, alkaline substance, urea, calcium carbonate, ammonia gas or the like to a predetermined pH within the range of, usually, 4 to 8. In cases where the feed rate of oxygen needs to be increased, this can be achieved by employing, for example, a method in which the oxygen concentration is maintained at not less than 21% by adding oxygen into the air, a method in which the culturing is carried out under pressure, a method in which the stirring rate is increased, or a method in which the ventilation volume is increased.

As the method for producing a chemical product using, as a fermentation feedstock, a purified sugar liquid obtained by the method of the present invention for producing a sugar liquid, fermentation culture methods known to those skilled in the art may be employed, and, in view of productivity, the continuous culture method disclosed in WO2007/097260 is preferably employed.

In the present invention, the chemical product produced by the method for producing a chemical product is not restricted as long as it is a substance produced in the culture liquid by the above microorganism or cells. Specific examples of the chemical product produced in the present invention include alcohols, organic acids, amino acids and nucleic acids, which are substances mass-produced in the fermentation industry. Examples the alcohols include ethanol, 1,3-propanediol, 1,4-propanediol and glycerol; examples of the organic acids include acetic acid, lactic acid, pyruvic acid, succinic acid, malic acid, itaconic acid and citric acid; examples of the nucleic acids include nucleosides such as inosine and guanosine, and nucleotides such as inosinic acid and guanylic acid; and diamine compounds such as cadaverine. Further, the present invention may also be applied to production of substances such as enzymes, antibiotics and recombinant proteins. FIGS. 1 and 2 are schematic views of major modes of the method for producing a sugar liquid of the present invention. These modes comprise: an enzymatic saccharification tank for hydrolyzing a pretreated product of a cellulose-containing biomass with a saccharifying enzyme to obtain an enzymatically saccharified liquid; a solid-liquid separation section for removal of undegraded residues; an anionic-polymer-adding section; a section for removal of contaminants from the sugar liquid, in which contaminants and enzymes are removed by filtration through a microfiltration membrane and/or ultrafiltration membrane; and a sugar liquid purification section, in which the sugar liquid is filtered through a nanofiltration membrane and/or reverse osmosis membrane for concentration/purification of the sugar liquid, to obtain a purified sugar liquid as the membrane non-permeate fraction.

EXAMPLES

The method of the present invention for producing a sugar liquid is described below in more detail by way of Examples. However, the present invention is not restricted to these Examples.
(1) Method for Measuring Weight Average Molecular Weights of Anionic Polymer, Polycarboxylic Acid and Polysulfonic Acid By gel permeation chromatography (GPC), the molecular weight was measured under the following conditions. Each sample was prepared such that its concentration was 0.1% by mass, and passed through a 0.45-μm filter before the measurement.
Column: Asahipak GF-7M (manufactured by Shodex)
Mobile phase: 50 mM sodium hydrogen phosphate (flow rate: 0.6 mL/min.)
Reaction liquid: None
Detection method: RI (differential refractive index)
Temperature: 40° C.
(2) Method for Measuring Weight Average Molecular Weights of Anionic Polymer and Polyphosphate Polymer By gel permeation chromatography (GPC), the molecular weight was measured under the following conditions. Each sample was prepared such that its concentration was 0.1% by mass, and passed through a 0.45-μm filter before the measurement.
Column: Asahipak GS-220HQ (manufactured by Shodex); two columns were linearly arranged
Mobile phase: 50 mM Sodium chloride (flow rate: 0.6 mL/min.)
Reaction liquid: None
Detection method: RI (differential refractive index)
Temperature: 60° C.
(3) Method for Measuring pH Using a handy pH meter "D-50" manufactured by Horiba, Ltd., the pH of the aqueous cellulose-derived sugar solution was measured. After stirring for measurement, 500-mL aliquots were collected in beakers, and measurement was carried out 3 times. The average of the measured values was used as the pH value.

Reference Example 1

Method for Measuring Monosaccharide Concentrations

Concentrations of monosaccharides (glucose concentration and xylose concentration) contained in the sugar liquid obtained in each of the Examples and Comparative Examples were analyzed by HPLC under the following conditions, and quantified based on comparison with standard samples.
Column: Luna $NH_2$ (manufactured by Phenomenex, Inc.)
Mobile phase: Ultrapure water:acetonitrile=25:75 (flow rate, 0.6 mL/min.)
Reaction liquid: None
Detection method: RI (differential refractive index)
Temperature: 30° C.

Reference Example 2

Method for Measuring Concentrations of Fermentation Inhibitors

Furan-based fermentation inhibitors (HMF and furfural) and phenol-based fermentation inhibitors (vanillin, acetovanillin, syringic acid, levulinic acid and 4-hydroxybenzoic acid) contained in the sugar liquid were analyzed by HPLC under the following conditions, and quantified based on comparison with standard samples.
Column: Synergi HidroRP 4.6 mm×250 mm (manufactured by Phenomenex, Inc.)
Mobile phase: acetonitrile—0.1 wt % $H_3PO_4$ (flow rate, 1.0 mL/min.)
Detection method: UV (283 nm)
Temperature: 40° C.

Among the fermentation inhibitors contained in the sugar liquid, organic acids (acetic acid and formic acid) were analyzed by HPLC under the following conditions, and quantified based on comparison with standard samples.
Column: Shim-Pack SPR-H and Shim-Pack SCR101H (manufactured by Shimadzu Corporation) that were linearly arranged
Mobile phase: 5 mM p-toluenesulfonic acid (flow rate, 0.8 mL/min.)
Reaction liquid: 5 mM p-toluenesulfonic acid, 20 mM Bis-Tris, 0.1 mM EDTA-2Na (flow rate, 0.8 mL/min.)
Detection method: Electric conductivity
Temperature: 45° C.

Reference Example 3

Step of Hydrolysis of Cellulose-containing Biomass by Dilute Sulfuric Acid/Enzyme Treatment The process of hydrolysis of a cellulose-containing biomass in Step (1) is described below by way of an example wherein 0.1 to 15% by weight of dilute sulfuric acid and an enzyme were used to hydrolyze a cellulose-containing biomass. As the cellulose-containing biomass, rice straw that was pulverized into 2-mm pieces was used. The cellulose-containing biomass was soaked in 1% aqueous sulfuric acid solution, and subjected to treatment using an autoclave (manufactured by Nitto Koatsu Co., Ltd.) at 150° C. for 30 minutes. Thereafter, solid-liquid separation was carried out to separate sulfuric acid-treated cellulose from the aqueous sulfuric acid solution. Subsequently, the sulfuric acid-treated cellulose was mixed with the dilute-sulfuric-acid treatment liquid with stirring such that the concentration of the solid matter was 10% by weight, and the pH was adjusted to about 5 with sodium hydroxide. To this mixture, Accellerase 1500 and XY (Genencor Kyowa) were added, to perform hydrolysis reaction with stirring at 50° C. for 1 day. Thereafter, solid-liquid separation was carried out using a filter press (manufactured by Yabuta Industries Co., Ltd., MO-4) for separating and removing undegraded cellulose or lignin, to obtain an aqueous solution containing sugars (hereinafter referred to as dilute-sulfuric-acid-treated saccharified liquid). The turbidity of the dilute-sulfuric-acid-treated enzymatically saccharified liquid was 70 NTU. The compositions of fermentation inhibitors and monosaccharides contained in the dilute-sulfuric-acid-treated enzymatically saccharified liquid were as shown in Tables 1 to 3.

TABLE 1

Quantification of fermentation inhibitors 1

|  | Formic acid | Acetic acid | HMF | Furfural |
|---|---|---|---|---|
| Dilute-sulfuric-acid-treated saccharified liquid | 0.1 g/L | 2.4 g/L | 125 mg/L | 875 mg/L |

TABLE 2

Quantification of fermentation inhibitors 2

|  | Vanillin | Coumaric acid | Ferulic acid |
|---|---|---|---|
| Dilute-sulfuric-acid-treated saccharified liquid | 55 mg/L | 150 mg/L | 75 mg/L |

TABLE 3

Quantification of monosaccharides

|  | Glucose | Xylose |
|---|---|---|
| Dilute-sulfuric-acid-treated saccharified liquid | 25 g/L | 12 g/L |

Reference Example 4

Step of Hydrolysis of Cellulose-containing Biomass by Hydrothermal Treatment and Enzyme Treatment The process of hydrolysis of a cellulose-containing biomass in Step (1) is described below by way of an example wherein subcritical water and an enzyme were used to hydrolyze a cellulose-containing biomass. As the cellulose-containing biomass, rice straw that was pulverized into 2-mm pieces was used. The cellulose-containing biomass was soaked in water, and subjected to treatment using an autoclave (manufactured by Nitto Koatsu Co., Ltd.) at 180° C. for 5 minutes with stirring. The pressure at that time was 10 MPa. Thereafter, solid-liquid separation of the processed biomass component was carried out by centrifugation (3000 G). To the resulting solution component, Accellerase DUET (Genencor Kyowa) was added, and the reaction was allowed to proceed at 50° C. for 24 hours, to obtain a sugar liquid derived from the solution component (hereinafter referred to as hydrothermally treated liquid). Thereafter, the water content in the processed biomass component was measured, and RO water was added to the sugar liquid such that the solid matter concentration was 10% by weight in terms of the absolute-drying-processed biomass, followed by adding Accellerase 1500 and XY (Genencor Kyowa) as cellulases thereto to perform hydrolysis reaction with stirring at 50° C. for 1 day. Thereafter, the resulting liquid was treated using a filter press (manufactured by Yabuta Industries Co., Ltd., MO-4) for separating and removing undegraded cellulose or lignin, to obtain a sugar liquid derived from the processed biomass (hereinafter referred to as hydrothermally treated saccharified liquid). The turbidity of the hydrothermally treated saccharified liquid was 10 NTU. The turbidity of the hydrothermally treated liquid was 800 NTU. The compositions of fermentation inhibitors and monosaccharides contained in the hydrothermally treated liquid and the hydrothermally treated enzymatically saccharified liquid were as shown in Tables 4 to 6.

TABLE 4

Quantification of fermentation inhibitors 1

|  | Formic acid | Acetic acid | HMF | Furfural |
|---|---|---|---|---|
| Hydrothermally treated liquid | 1.1 g/L | 2.2 g/L | 120 mg/L | 500 mg/L |
| Hydrothermally treated saccharified liquid | 0.1 g/L | 0.4 g/L | 6 mg/L | 10 mg/L |

TABLE 5

Quantification of fermentation inhibitors 2

|  | Vanillin | Coumaric acid | Ferulic acid |
|---|---|---|---|
| Hydrothermally treated liquid | 50 mg/L | 200 mg/L | 130 mg/L |
| Hydrothermally treated saccharified liquid | 2 mg/L | 10 mg/L | 6 mg/L |

TABLE 6

| | Glucose | Xylose |
|---|---|---|
| Hydrothermally treated liquid | 7 g/L | 15 g/L |
| Hydrothermally treated saccharified liquid | 40 g/L | 10 g/L |

Reference Example 5

Step of Ammonia Treatment of Cellulose-containing Biomass Followed by Enzymatic Hydrolysis The process of hydrolysis of a cellulose-containing biomass in Step (1) is described below by way of an example wherein 5.0 to 100% by weight of aqueous ammonia and an enzyme were used to hydrolyze a cellulose-containing biomass. As the cellulose-containing biomass, rice straw that was pulverized into 2-mm pieces was used. The cellulose-containing biomass was fed to a compact reactor (manufactured by Taiatsu Techno Corporation, TVS-N2 30 mL), and cooled with liquid nitrogen. Into this reactor, ammonia gas was flown, and the sample was completely soaked in liquid ammonia. The lid of the reactor was closed, and the reactor was left to stand at room temperature for about 15 minutes. Subsequently, the reactor was processed in an oil bath at 150° C. for 30 minutes. Thereafter, the reactor was removed from the oil bath, and the ammonia gas was leaked in a fume hood, followed by vacuuming the inside of the reactor to 10 Pa with a vacuum pump, thereby drying the cellulose-containing biomass. The processed cellulose-containing biomass was mixed with pure water by stirring such that the concentration of the solid matter was 15% by weight, and the pH was adjusted to about 5 with sulfuric acid. To this mixture, Accellerase 1500 and XY (Genencor Kyowa) were added, to perform hydrolysis reaction with stirring at 50° C. for 1 day. Thereafter, filter press treatment was carried out for separating and removing undegraded cellulose and lignin, to obtain an aqueous solution containing sugars (hereinafter referred to as ammonia-treated saccharified liquid). The turbidity of the ammonia-treated sugar liquid was 25 NTU. The compositions of fermentation inhibitors and monosaccharides contained in the ammonia-treated enzymatically saccharified liquid were as shown in Tables 7 to 9.

TABLE 7

Quantification of fermentation inhibitors 1

| | Formic acid | Acetic acid | HMF | Furfural |
|---|---|---|---|---|
| Ammonia-treated saccharified liquid | 1.1 g/L | 0.5 g/L | 12 mg/L | 5 mg/L |

TABLE 8

Quantification of fermentation inhibitors 2

| | Vanillin | Coumaric acid | Ferulic acid |
|---|---|---|---|
| Ammonia-treated saccharified liquid | 20 mg/L | 18 mg/L | 2 mg/L |

TABLE 9

Quantification of monosaccharides

| | Glucose | Xylose |
|---|---|---|
| Ammonia-treated saccharified liquid | 40 g/L | 24 g/L |

Example 1

Addition of Anionic Polymer

The dilute-sulfuric-acid-treated saccharified liquid obtained in Reference Example 3 was filtered through a microfiltration membrane (Stericup, manufactured by Millipore, pore size, 0.22 μm). The obtained filtrate was divided into 500-mL aliquots, and sodium tripolyphosphate (weight average molecular weight: 368, manufactured by Kanto Chemical Co., Ltd.), which is an inorganic polyphosphate, or sodium polyacrylate (weight average molecular weight: 2000 by GPC, manufactured by Sigma Aldrich), which is a polycarboxylate, was added thereto as an anionic polymer at 5 mg/L. Each liquid obtained by addition of the polymer was subjected to a membrane permeation test using a flat membrane unit SEPA CF-II (manufactured by GE Osmonics), which can be used as a compact filtration tester for a spiral-wound module. As the membrane, a nanofiltration membrane GE SEPA-DK series (manufactured by GE Osmonics) or an ultra-low pressure RO membrane UTC70U was used. The permeability test was carried out under the conditions of a surface linear velocity of 20 cm/sec. and a filtration flux of 0.2 m/D. The results are shown in Table 10 (for the cases where a nanofiltration membrane was used) and Table 11 (for the cases where an ultra-low pressure RO membrane was used). In these tables, the permeation rates (%) of glucose, formic acid, acetic acid, furfural and ferulic acid are values calculated by actually measuring their concentrations in the permeate side and dividing the measured values by the concentrations shown in the above Reference Examples, followed by multiplying the obtained values by 100. The measurement was carried out at a constant temperature of 25° C. after confirming that the pH change by the addition of the polymer was less than 0.05. As a result, it was found that addition of sodium tripolyphosphate or sodium polyacrylate as an aqueous anionic polymer solution increases the permeation rates of formic acid, acetic acid and ferulic acid, as compared to the later-described Comparative Example 1, in which these polymers were not added.

TABLE 10

Use of a nanofiltration membrane

| Additive | Name of dissolved substance | Permeation rate |
|---|---|---|
| Sodium tripolyphosphate | Glucose | 3% |
| | Formic acid | 90% |
| | Acetic acid | 86% |
| | Furfural | 98% |
| | Ferulic acid | 64% |
| Sodium polyacrylate | Glucose | 3% |
| | Formic acid | 88% |
| | Acetic acid | 82% |
| | Furfural | 98% |
| | Ferulic acid | 64% |

TABLE 11

Use of an ultra-low pressure RO membrane

| Additive | Name of dissolved substance | Permeation rate |
|---|---|---|
| Sodium tripolyphosphate | Glucose | 0.50% |
| | Formic acid | 84% |
| | Acetic acid | 70% |
| | Furfural | 50% |
| | Ferulic acid | 15% |
| Sodium polyacrylate | Glucose | 0.50% |
| | Formic acid | 80% |
| | Acetic acid | 66% |
| | Furfural | 50% |
| | Ferulic acid | 14% |

Comparative Example 1

No Addition of Polymer, or Addition of Cationic Polymer

The filtrate obtained by microfiltration membrane treatment in Example 1 was divided into 500-mL aliquots, and no polymer was added thereto, or polyethyleneimine (weight average molecular weight, about 600; manufactured by Wako Pure Chemical Industries, Ltd.) as a cationic polymer was added thereto at 5 mg/L. Each liquid obtained by addition or without addition of the polymer was subjected to a membrane permeation test using a flat membrane unit SEPA CF-II (manufactured by GE Osmonics), which can be used as a compact filtration tester for a spiral-wound module. As the membrane, a nanofiltration membrane GE SEPA-DK series (manufactured by GE Osmonics) or an ultra-low pressure RO membrane UTC70U (manufactured by Toray Industries, Inc.) was used. The permeability test was carried out under the conditions of a surface linear velocity of 20 cm/sec. and a filtration flux of 0.5 m/D. The results are shown in Table 12 and Table 13. In these tables, the permeation rates (%) of glucose, formic acid, acetic acid, furfural and coumaric acid are values calculated by actually measuring their concentrations in the permeate side and dividing the measured values by the concentrations shown in the above Reference Examples, followed by multiplying the obtained values by 100. The measurement was carried out at a constant temperature of 25° C. after confirming that the pH change by the addition of the polymer was less than 0.05. As a result, it was found that the cases without addition of a polymer showed lower permeation rates of formic acid, acetic acid and ferulic acid than the cases of Example 1, wherein an anionic polymer was added, and that the cases where the cationic polymer polyethyleneimine was added showed even lower permeation rates of formic acid, acetic acid and ferulic acid than the cases without addition of a polymer.

TABLE 12

Use of a nanofiltration membrane

| Additive | Name of dissolved substance | Permeation rate |
|---|---|---|
| None | Glucose | 3% |
| | Formic acid | 82% |
| | Acetic acid | 76% |
| | Furfural | 98% |
| | Ferulic acid | 60% |

TABLE 12-continued

Use of a nanofiltration membrane

| Additive | Name of dissolved substance | Permeation rate |
|---|---|---|
| Polyethyleneimine | Glucose | 2% |
| | Formic acid | 75% |
| | Acetic acid | 70% |
| | Furfural | 94% |
| | Ferulic acid | 56% |

TABLE 13

Use of a reverse filtration membrane

| Additive | Name of dissolved substance | Permeation rate |
|---|---|---|
| None | Glucose | 0.50% |
| | Formic acid | 75% |
| | Acetic acid | 60% |
| | Furfural | 50% |
| | Ferulic acid | 10% |
| Polyethyleneimine | Glucose | 0.50% |
| | Formic acid | 70% |
| | Acetic acid | 52% |
| | Furfural | 48% |
| | Ferulic acid | 8% |

Example 2

Each of the hydrothermally treated liquid and the hydrothermally treated saccharified liquid obtained in Reference Example 4 was filtered through a microfiltration membrane (Stericup, manufactured by Millipore, pore size, 0.22 µm). Since large-scale processing of the hydrothermally treated liquid with the microfiltration membrane was difficult, its filtration treatment was carried out while the membrane surface was washed after filtration of every 100 mL. The obtained filtrate was divided into 500-mL aliquots, and, similarly to Example 1, sodium tripolyphosphate or sodium polyacrylate was added thereto at 5 mg/L. Similarly to Example 1, each liquid obtained by addition of the polymer was subjected to a membrane permeation test using a flat membrane unit SEPA CF-II (manufactured by GE Osmonics). As the membrane, a nanofiltration membrane GE SEPA-DK series (manufactured by GE Osmonics) was used. The permeability test was carried out under the conditions of a surface linear velocity of 20 cm/sec. and a filtration flux of 0.2 m/D. The results are shown in Table 14 (for the results of filtration of the hydrothermally treated liquid) and Table 15 (for the results of filtration of the hydrothermally treated saccharified liquid). In these tables, the permeation rate (%) of glucose is a value calculated by actually measuring its concentration in the permeate side and dividing the measured value by the concentration shown in the above Reference Examples, followed by multiplying the obtained value by 100. The measurement was carried out at a constant temperature of 25° C. after confirming that the pH change by the addition of the polymer was less than 0.05. As a result, it was found that addition of especially sodium tripolyphosphate as an aqueous anionic polymer solution to the sugar liquid before the nanofiltration membrane treatment increases the permeation rates of formic acid, acetic acid and ferulic acid as compared to Comparative Example 2 in which the polymer was not added. Further, sodium polyacrylate was also effective for improvement of these permeation rates, although the effect was smaller than that of sodium tripolyphosphate.

TABLE 14

Results of filtration of hydrothermally treated liquid

| Additive | Name of dissolved substance | Permeation rate |
|---|---|---|
| Sodium tripolyphosphate | Glucose | 3% |
|  | Formic acid | 96% |
|  | Acetic acid | 90% |
|  | Furfural | 96% |
|  | Ferulic acid | 72% |
| Sodium polyacrylate | Glucose | 2% |
|  | Formic acid | 85% |
|  | Acetic acid | 75% |
|  | Furfural | 96% |
|  | Ferulic acid | 60% |

TABLE 15

Results of filtration of hydrothermally treated saccharified liquid

| Additive | Name of dissolved substance | Permeation rate |
|---|---|---|
| Sodium tripolyphosphate | Glucose | 2% |
|  | Formic acid | 90% |
|  | Acetic acid | 86% |
|  | Furfural | 100% |
|  | Ferulic acid | 70% |
| Sodium polyacrylate | Glucose | 2% |
|  | Formic acid | 84% |
|  | Acetic acid | 78% |
|  | Furfural | 96% |
|  | Ferulic acid | 60% | cationic polymer polyethyleneimine is not effective for, or leads to a low permeation rate of, any of the substances.

TABLE 16

Results of filtration of hydrothermally treated liquid

| Additive/amount | Name of dissolved substance | Permeation rate |
|---|---|---|
| None | Glucose | 2% |
|  | Formic acid | 80% |
|  | Acetic acid | 74% |
|  | Furfural | 96% |
|  | Ferulic acid | 60% |
| Polyethyleneimine 5 mg/L | Glucose | 2% |
|  | Formic acid | 70% |
|  | Acetic acid | 65% |
|  | Furfural | 92% |
|  | Ferulic acid | 50% |

TABLE 17

Results of filtration of hydrothermally treated saccharified liquid

| Additive/amount | Name of dissolved substance | Permeation rate |
|---|---|---|
| None | Glucose | 3% |
|  | Formic acid | 80% |
|  | Acetic acid | 76% |
|  | Furfural | 98% |
|  | Ferulic acid | 60% |
| Polyethyleneimine 5 mg/L | Glucose | 2% |
|  | Formic acid | 80% |
|  | Acetic acid | 62% |
|  | Furfural | 94% |
|  | Ferulic acid | 50% |

Comparative Example 2

Each filtrate obtained by microfiltration membrane treatment in Example 2 was divided into 500-mL aliquots, and no polymer was added thereto, or polyethyleneimine as a cationic polymer was added thereto at 5 mg/L. Each liquid obtained by addition or without addition of the polymer was subjected to a membrane permeation test using a flat membrane unit SEPA CF-II (manufactured by GE Osmonics), which can be used as a compact filtration tester for a spiral-wound module. As the membrane, a nanofiltration membrane GE SEPA-DK series (manufactured by GE Osmonics) or an ultra-low pressure RO membrane UTC70U (manufactured by Toray Industries, Inc.) was used. The permeability test was carried out under the conditions of a surface linear velocity of 20 cm/sec. and a filtration flux of 0.5 m/D. The results are shown in Table 16 and Table 17. In these tables, the permeation rates (%) of glucose, formic acid, acetic acid, furfural and coumaric acid are values calculated by actually measuring their concentrations in the permeate side and dividing the measured values by the concentrations shown in the above Reference Examples, followed by multiplying the obtained values by 100. The measurement was carried out at a constant temperature of 25° C. after confirming that the pH change by the addition of the polymer was less than 0.05. As a result, it was found that the permeation rates of formic acid, acetic acid and ferulic acid were worse than those in Example 2, in which an anionic polymer was added before filtration with a nanofiltration membrane. Further, it was found that addition of the Example 3

Each ammonia-treated saccharified liquid obtained in Reference Example 5 was filtered through a microfiltration membrane (Stericup, manufactured by Millipore; pore size, 0.22 μm). The obtained filtrate was divided into 500-mL aliquots, and sodium tripolyphosphate, which is an inorganic phosphate polymer, or sodium polyacrylate, which is a polycarboxylate polymer, was added thereto as an anionic polymer at 5 mg/L or 50 mg/L. Each liquid obtained by addition of the polymer was subjected to a membrane permeation test using a flat membrane unit SEPA CF-II (manufactured by GE Osmonics), which can be used as a compact filtration tester for a spiral-wound module. As the membrane, an ultra-low pressure RO membrane UTC70U was used. The permeability test was carried out under the conditions of a surface linear velocity of 20 cm/sec. and a filtration flux of 0.2 m/D. The results are shown in Table 18. In this table, the permeation rates (%) of glucose, formic acid, acetic acid, furfural and ferulic acid are values calculated by actually measuring their concentrations in the permeate side and dividing the measured values by the concentrations shown in the above Reference Examples, followed by multiplying the obtained values by 100. The measurement was carried out at a constant temperature of 25° C. after confirming that the pH change by the addition of the polymer was less than 0.05. As a result, it was found that addition of sodium tripolyphosphate or sodium polyacrylate as an aqueous anionic polymer solution to the sugar liquid before the reverse osmosis membrane treatment increases the permeation rates of formic acid, acetic acid and ferulic acid as compared to Comparative Example 3, in which these polymers were not added.

TABLE 18

Results of filtration through an ultra-low pressure RO membrane (ammonia treatment)

| Additive/amount | Name of dissolved substance | Permeation rate |
|---|---|---|
| Sodium tripolyphosphate 5 mg/L | Glucose | 0.50% |
| | Formic acid | 90% |
| | Acetic acid | 75% |
| | Furfural | 53% |
| | Ferulic acid | 20% |
| Sodium polyacrylate 5 mg/L | Glucose | 0.50% |
| | Formic acid | 80% |
| | Acetic acid | 70% |
| | Furfural | 50% |
| | Ferulic acid | 15% |
| Sodium tripolyphosphate 50 mg/L | Glucose | 0.50% |
| | Formic acid | 87% |
| | Acetic acid | 72% |
| | Furfural | 50% |
| | Ferulic acid | 18% |
| Sodium polyacrylate 50 mg/L | Glucose | 0.50% |
| | Formic acid | 76% |
| | Acetic acid | 65% |
| | Furfural | 50% |
| | Ferulic acid | 12% |

Comparative Example 3

The filtrate obtained by microfiltration membrane treatment in Example 3 was divided into 500-mL aliquots, and no polymer was added thereto, or polyethyleneimine as a cationic polymer was added thereto at 5 mg/L or not more than 50 mg/L. Each liquid obtained by addition or without addition of the polymer was subjected to a membrane permeation test using a flat membrane unit SEPA CF-II (manufactured by GE Osmonics), which can be used as a compact filtration tester for a spiral-wound module. As the membrane, a nanofiltration membrane GE SEPA-DK series (manufactured by GE Osmonics) or an ultra-low pressure RO membrane UTC70U (manufactured by Toray Industries, Inc.) was used. The permeability test was carried out under the conditions of a surface linear velocity of 20 cm/sec. and a filtration flux of 0.5 m/D. The results are shown in Table 19. In this table, the permeation rates (%) of glucose, formic acid, acetic acid, furfural and coumaric acid are values calculated by actually measuring their concentrations in the permeate side and dividing the measured values by the concentrations shown in the above Reference Examples, followed by multiplying the obtained values by 100. The measurement was carried out at a constant temperature of 25° C. after confirming that the pH change by the addition of the polymer was less than 0.05. As a result, it was found that the permeation rates of formic acid, acetic acid and ferulic acid were worse than those in Example 3, in which an anionic polymer was added before filtration with a nanofiltration membrane. Further, it was found that addition of the cationic polymer polyethyleneimine is not effective for, or leads to a low permeation rate of, any of the substances.

TABLE 19

Use of a reverse filtration membrane

| Additive/amount | Name of dissolved substance | Permeation rate |
|---|---|---|
| None | Glucose | 0.50% |
| | Formic acid | 75% |
| | Acetic acid | 60% |
| | Furfural | 50% |
| | Ferulic acid | 10% |
| Polyethyleneimine 5 mg/L | Glucose | 0.30% |
| | Formic acid | 70% |
| | Acetic acid | 52% |
| | Furfural | 45% |
| | Ferulic acid | 7% |
| Polyethyleneimine 50 mg/L | Glucose | 0.20% |
| | Formic acid | 65% |
| | Acetic acid | 50% |
| | Furfural | 40% |
| | Ferulic acid | 5% |

Example 4

The ammonia-treated saccharified liquid obtained in Reference Example 5 was filtered through a microfiltration membrane (Stericup, manufactured by Millipore; pore size, 0.22 µm). The obtained filtrate was divided into 500-mL aliquots, and, similarly to Example 1, sodium tripolyphosphate or sodium polyacrylate was added thereto as an anionic polymer at 0.05 g/L or 500 mg/L. Each liquid obtained by addition of the polymer was subjected to a membrane permeation test using a flat membrane unit SEPA CF-II (manufactured by GE Osmonics), which can be used as a compact filtration tester for a spiral-wound module. As the membrane, an ultra-low pressure RO membrane UTC70U was used. The permeability test was carried out under the conditions of a surface linear velocity of 20 cm/sec. and a filtration flux of 0.2 m/D. The results are shown in Table 18. In this table, the permeation rates (%) of glucose, formic acid, acetic acid, furfural and ferulic acid are values calculated by actually measuring their concentrations in the permeate side and dividing the measured values by the concentrations shown in the above Reference Examples, followed by multiplying the obtained values by 100. The measurement was carried out at a constant temperature of 25° C. after confirming that the pH change by the addition of the polymer was less than 0.05. As a result, it was found that addition of sodium tripolyphosphate or sodium polyacrylate as an aqueous anionic polymer solution to the sugar liquid at 0.05 mg/L or 500 mg/L before the reverse osmosis membrane treatment increases the permeation rates of formic acid, acetic acid and ferulic acid as compared to Comparative Example 3, in which these polymers were not added, although the effects were smaller than those of Example 3, in which the concentration was 0.05 mg/L or 500 mg/L

TABLE 20

Results of filtration through an ultra-low pressure RO membrane (ammonia treatment, addition of different amounts of polymers)

| Additive/amount | Name of dissolved substance | Permeation rate |
|---|---|---|
| Sodium tripolyphosphate 0.05 mg/L | Glucose | 0.50% |
| | Formic acid | 80% |
| | Acetic acid | 66% |
| | Furfural | 50% |
| | Ferulic acid | 12% |

TABLE 20-continued

Results of filtration through an ultra-low pressure RO membrane (ammonia treatment, addition of different amounts of polymers)

| Additive/amount | Name of dissolved substance | Permeation rate |
|---|---|---|
| Sodium polyacrylate 0.05 mg/L | Glucose | 0.50% |
| | Formic acid | 78% |
| | Acetic acid | 64% |
| | Furfural | 50% |
| | Ferulic acid | 12% |
| Sodium tripolyphosphate 500 mg/L | Glucose | 0.50% |
| | Formic acid | 86% |
| | Acetic acid | 70% |
| | Furfural | 50% |
| | Ferulic acid | 15% |
| Sodium polyacrylate 500 mg/L | Glucose | 0.50% |
| | Formic acid | 80% |
| | Acetic acid | 64% |
| | Furfural | 50% |
| | Ferulic acid | 12% |

Example 5

The ammonia-treated saccharified liquid obtained in Reference Example 5 was filtered through a microfiltration membrane (Stericup, manufactured by Millipore; pore size, 0.22 μm). The obtained filtrate was divided into 500-mL aliquots, and, similarly to Example 1, sodium tripolyphosphate or sodium polyacrylate was added thereto as an anionic polymer at 0.005 mg/L or 5 g/L. Each liquid obtained by addition of the polymer was subjected to a membrane permeation test using a flat membrane unit SEPA CF-II (manufactured by GE Osmonics), which can be used as a compact filtration tester for a spiral-wound module. As the membrane, an ultra-low pressure RO membrane UTC70U was used. The permeability test was carried out under the conditions of a surface linear velocity of 20 cm/sec. and a filtration flux of 0.2 m/D. The results are shown in Table 18. In this table, the permeation rates (%) of glucose, formic acid, acetic acid, furfural and ferulic acid are values calculated by actually measuring their concentrations in the permeate side and dividing the measured values by the concentrations shown in the above Reference Examples, followed by multiplying the obtained values by 100. The measurement was carried out at a constant temperature of 25° C. after confirming that the pH change by the addition of the polymer was less than 0.05. As a result, addition of sodium tripolyphosphate or sodium polyacrylate as an aqueous anionic polymer solution to the sugar liquid at 0.005 g/L before the reverse osmosis membrane treatment was effective for the permeability to some extent, although the effect was smaller than that of Example 3. On the other hand, their addition at 5 g/L was effective, but no improvement in the effect could be observed as compared to the addition at 500 mg/L or less in Example 4.

TABLE 21

Results of filtration through an ultra-low pressure RO membrane (ammonia treatment)

| Additive/amount | Name of dissolved substance | Permeation rate |
|---|---|---|
| Sodium tripolyphosphate 0.005 mg/L | Glucose | 0.50% |
| | Formic acid | 75% |
| | Acetic acid | 62% |
| | Furfural | 50% |
| | Ferulic acid | 10% |

TABLE 21-continued

Results of filtration through an ultra-low pressure RO membrane (ammonia treatment)

| Additive/amount | Name of dissolved substance | Permeation rate |
|---|---|---|
| Sodium polyacrylate 0.005 mg/L | Glucose | 0.50% |
| | Formic acid | 75% |
| | Acetic acid | 62% |
| | Furfural | 50% |
| | Ferulic acid | 10% |
| Sodium tripolyphosphate 5 g/L | Glucose | 0.50% |
| | Formic acid | 86% |
| | Acetic acid | 70% |
| | Furfural | 50% |
| | Ferulic acid | 15% |
| Sodium polyacrylate 5 g/L | Glucose | 0.50% |
| | Formic acid | 80% |
| | Acetic acid | 64% |
| | Furfural | 50% |
| | Ferulic acid | 12% |

Example 6

In the same manner as in Example 2, each of the hydrothermally treated liquid and hydrothermally treated saccharified liquid obtained in Reference Example 4 was filtered through a microfiltration membrane (Stericup, manufactured by Millipore, pore size, 0.22 μm). The obtained filtrate was divided into 500-mL aliquots, and sodium hexametaphosphate (weight average molecular weight, 612; manufactured by Sigma Aldrich), poly(acrylic acid-co-maleic acid) (weight average molecular weight, 3000; manufactured by Sigma Aldrich) or sodium polyacrylate (weight average molecular weight, 8000, manufactured by Sigma Aldrich) was added thereto as a phosphate polymer at 5 mg/L. Each liquid obtained by addition of the polymer was subjected to a membrane permeation test using a flat membrane unit SEPA CF-II (manufactured by GE Osmonics) in the same manner as in Example 1. As the membrane, a nanofiltration membrane GE SEPA-DK series (manufactured by GE Osmonics) was used. The permeability test was carried out under the conditions of a surface linear velocity of 20 cm/sec. and a filtration flux of 0.2 m/D. The results are shown in Table 22 (results of filtration of the hydrothermally treated liquid) and Table 23 (results of filtration of the hydrothermally treated saccharified liquid). In these tables, the permeation rate (%) of glucose is a value calculated by actually measuring its concentration in the permeate side and dividing the measured value by the concentration shown in the above Reference Examples, followed by multiplying the obtained values by 100. The measurement was carried out at a constant temperature of 25° C. after confirming that the pH change by the addition of the polymer was less than 0.05. As a result, it was found that addition of sodium hexametaphosphate, poly(acrylic acid-co-maleic acid) or sodium polyacrylate as an aqueous anionic polymer solution to the sugar liquid before the nanofiltration membrane treatment increases the permeation rates of formic acid, acetic acid and coumaric acid as compared to Comparative Example 2 in which the nanofiltration membrane treatment was carried out without addition of any polymer.

TABLE 22

Results of filtration of hydrothermally treated liquid

| Additive | Name of dissolved substance | Permeation rate |
|---|---|---|
| Sodium hexametaphosphate | Glucose | 3% |
| | Formic acid | 98% |
| | Acetic acid | 92% |
| | Furfural | 96% |
| | Ferulic acid | 80% |
| Poly(acrylic acid-co-maleic acid) | Glucose | 2% |
| | Formic acid | 90% |
| | Acetic acid | 80% |
| | Furfural | 96% |
| | Ferulic acid | 70% |
| Sodium polyacrylate (weight average molecular weight, 8000) | Glucose | 2% |
| | Formic acid | 90% |
| | Acetic acid | 80% |
| | Furfural | 98% |
| | Ferulic acid | 70% |

TABLE 23

Results of filtration of hydrothermally treated saccharified liquid

| Additive | Name of dissolved substance | Permeation rate |
|---|---|---|
| Sodium hexametaphosphate | Glucose | 3% |
| | Formic acid | 92% |
| | Acetic acid | 86% |
| | Furfural | 100% |
| | Ferulic acid | 72% |
| Poly(acrylic acid-co-maleic acid) | Glucose | 2% |
| | Formic acid | 84% |
| | Acetic acid | 80% |
| | Furfural | 96% |
| | Ferulic acid | 64% |
| Sodium polyacrylate (weight average molecular weight, 8000) | Glucose | 2% |
| | Formic acid | 84% |
| | Acetic acid | 78% |
| | Furfural | 96% |
| | Ferulic acid | 60% |

Example 7

Addition of Both Sodium Polyacrylate and Polyphosphate

The hydrothermally treated liquid obtained in Reference Example 4 was filtered through a microfiltration membrane (Stericup, manufactured by Millipore, pore size, 0.22 μm) while the membrane surface was washed after filtration of every 100 mL, to perform filtration treatment. To the obtained filtrate, sodium tripolyphosphate (weight average molecular weight: 368) (manufactured by Rin Kagaku Kogyo Co., Ltd.) and sodium polyacrylate (weight average molecular weight: 2000) (manufactured by Wako Pure Chemical Industries, Ltd.) were added such that each of these was contained at 5 mg/L. The liquid obtained by addition of the polymers was subjected to a membrane permeation test using a flat membrane unit SEPA CF-II (manufactured by GE Osmonics) in the same manner as in Example 1. As the membrane, a nanofiltration membrane GE SEPA-DK series (manufactured by GE Osmonics) was used. The permeability test was carried out under the conditions of a surface linear velocity of 20 cm/sec. and a filtration flux of 0.2 m/D. The results are shown in Table 24. In this table, the permeation rate (%) of glucose is a value calculated by actually measuring its concentration in the permeate side and dividing the measured value by the concentration shown in the above Reference Examples, followed by multiplying the obtained values by 100. The measurement was carried out at a constant temperature of 25° C. after confirming that the pH change by the addition of the polymer was less than 0.05. As a result, it was found that adding both sodium tripolyphosphate and sodium polyacrylate as aqueous anionic polymer solutions to the sugar liquid before the nanofiltration membrane treatment increases the permeation rates of formic acid, acetic acid and ferulic acid, which are organic acids, as compared to Comparative Example 2 (Table 16) in which no polymer was added.

TABLE 24

Results of filtration of hydrothermally treated liquid

| Additive | Name of dissolved substance | Permeation rate |
|---|---|---|
| Sodium tripolyphosphate/ Sodium polyacrylate Mixture | Glucose | 2% |
| | Formic acid | 96% |
| | Acetic acid | 90% |
| | Furfural | 96% |
| | Ferulic acid | 75% |

Comparative Example 4

Addition of Water-Insoluble Anionic Polymer

The hydrothermally treated liquid obtained in Reference Example 4 was filtered through a microfiltration membrane (Stericup, manufactured by Millipore, pore size, 0.22 μm) while the membrane surface was washed after filtration of every 100 mL, to perform filtration treatment. To the obtained filtrate, 5 mg of DIAION SK110 (manufactured by Mitsubishi Chemical Corporation), which is used as an ion-exchange resin, was added as a water-insoluble anionic polymer, and it was confirmed that the polymer was not dissolved. The liquid obtained after the addition was subjected to a membrane permeation test using a flat membrane unit SEPA CF-II (manufactured by GE Osmonics) in the same manner as in Example 1. As the membrane, a nanofiltration membrane GE SEPA-DK series (manufactured by GE Osmonics) was used. The permeability test was carried out under the conditions of a surface linear velocity of 20 cm/sec. and a filtration flux of 0.2 m/D. However, since the operating pressure increased immediately after the start of filtration, the filtration was terminated. When the flat membrane unit was opened and the membrane surface was observed, attachment of SK110 to the membrane surface and to the spacer mesh was found, so that it was found that a water-insoluble anionic polymer cannot be used.

Example 8

Changing pH

The hydrothermally treated saccharified liquid obtained in Reference Example 4 was filtered through a microfiltration membrane (Stericup, manufactured by Millipore, pore size, 0.22 μm). The obtained filtrate was divided into 500-mL aliquots, and sodium tripolyphosphate or sodium polyacrylate was added thereto at 5 mg/L. Thereafter, sulfuric acid or sodium hydroxide was added to the resulting mixture to adjust the pH to 3, 4, 5, 9 or 11, and each resulting liquid was subjected to a membrane permeation test using a flat membrane unit SEPA CF-II (manufactured by GE Osmonics) in the same manner as in Example 1. As the membrane, a nanofiltration membrane GE SEPA-DK series (manufactured by GE Osmonics) was used. The permeability test was carried out under the conditions of a surface linear velocity of 20 cm/sec. and a filtration flux of 0.2 m/D. The results are shown in Table 25. The operating pressure in the test is also shown in the table. In this table, the permeation rate (%) of glucose is a value calculated by actually measuring its concentration in the permeate side and dividing the measured value by the concentration shown in the above Reference Examples, followed by multiplying the obtained values by 100. The measurement was carried out at a constant temperature of 25° C. after confirming that the pH change by the addition of the polymer was less than 0.05.

TABLE 25

| Additive | Name of dissolved substance | Permeation rate | | | | |
|---|---|---|---|---|---|---|
| | | pH 3 | pH 4 | pH 5 | pH 9 | pH 11 |
| Sodium tripolyphosphate | Glucose | 1% | 2% | 2% | 2% | 2% |
| | Formic acid | 100% | 100% | 90% | 50% | 30% |
| | Acetic acid | 100% | 92% | 86% | 36% | 25% |
| | Furfural | 88% | 95% | 100% | 100% | 100% |
| | Ferulic acid | 88% | 84% | 70% | 42% | 15% |
| | Operating pressure | 2.5 MPa | 2.2 MPa | 2.1 MPa | 2.3 MPa | 2.3 MPa |
| Sodium polyacrylate | Glucose | 1% | 2% | 2% | 2% | 2% |
| | Formic acid | 100% | 100% | 84% | 50% | 84% |
| | Acetic acid | 100% | 92% | 78% | 36% | 78% |
| | Furfural | 88% | 95% | 96% | 100% | 96% |
| | Ferulic acid | 88% | 84% | 60% | 42% | 15% |
| | Operating pressure | 2.5 MPa | 2.2 MPa | 2.1 MPa | 2.3 MPa | 2.3 MPa |

Comparative Example 5

Changing pH (Addition of No Anionic Polymer)

The hydrothermally treated saccharified liquid obtained in Reference Example 4 was filtered through a microfiltration membrane (Stericup, manufactured by Millipore, pore size, 0.22 μm). The obtained filtrate was divided into 500-mL aliquots. Sulfuric acid or sodium hydroxide was added to each aliquot to adjust the pH to 3, 4, 5, 9 or 11, and each resulting liquid was subjected to a membrane permeation test using a flat membrane unit SEPA CF-II (manufactured by GE Osmonics) in the same manner as in Example 1. As the membrane, a nanofiltration membrane GE SEPA-DK series (manufactured by GE Osmonics) was used. The permeability test was carried out under the conditions of a surface linear velocity of 20 cm/sec. and a filtration flux of 0.2 m/D. The results are shown in Table 26. The operating pressure in the test is also shown in the table. In this table, the permeation rate (%) of glucose is a value calculated by actually measuring its concentration in the permeate side and dividing the measured value by the concentration shown in the above Reference Examples, followed by multiplying the obtained values by 100. The measurement was carried out at a constant temperature of 25° C. after confirming that the pH change by the addition of the polymer was less than 0.05.

TABLE 26

| Additive/amount | Name of dissolved substance | Permeation rate | | | | |
|---|---|---|---|---|---|---|
| | | pH 3 | pH 4 | pH 5 | pH 9 | pH 11 |
| None | Glucose | 2% | 3% | 3% | 3% | 4% |
| | Formic acid | 100% | 92% | 80% | 33% | 30% |
| | Acetic acid | 100% | 88% | 76% | 25% | 25% |
| | Furfural | 88% | 95% | 98% | 100% | 100% |
| | Ferulic acid | 88% | 72% | 60% | 20% | 15% |
| | Operating pressure | 3.2 MPa | 2.7 MPa | 2.2 MPa | 2.7 MPa | 2.7 MPa |

INDUSTRIAL APPLICABILITY

By the present invention, fermentation inhibitors can be efficiently removed from an aqueous sugar solution derived from a cellulose-containing biomass, and, on the other hand, a purified sugar liquid containing monosaccharides such as glucose and xylose can be produced at high purity and at high yield, so that use of the purified sugar liquid as a fermentation feedstock enables enhancement of the efficiencies of fermentative production of various chemical products.

DESCRIPTION OF SYMBOLS

1 Enzymatic saccharification
2 Solid-liquid separation
3 Anionic polymer
4 Microfiltration membrane and/or ultrafiltration membrane
5 Nanofiltration membrane and/or reverse osmosis membrane
6 Sugar liquid
7 Fermentation inhibitor

The invention claimed is:

1. A method of producing a sugar liquid comprising concentrating an aqueous cellulose-derived sugar solution with a nanofiltration membrane and/or reverse osmosis membrane, wherein said concentration is carried out after adding a water-soluble anionic polymer to said aqueous cellulose-derived sugar solution to increase the passage of one or more fermentation inhibitors into the permeate side of said nanofiltration membrane and/or reverse osmosis membrane.

2. The method according to claim 1, wherein said aqueous cellulose-derived sugar solution to be concentrated with said nanofiltration membrane and/or reverse osmosis membrane is a permeate of a microfiltration membrane and/or ultrafiltration membrane.

3. The method according to claim 1, wherein said water-soluble anionic polymer comprises a polymer selected from the group consisting of a salt of a phosphate polymer, a phosphate polymer, a salt of a polycarboxylate polymer and a polycarboxylate polymer.

4. The method according to claim 1, wherein said water-soluble anionic polymer is an inorganic polyphosphate.

5. The method according to claim 1, wherein the pH of said aqueous cellulose-derived sugar solution after addition of said water-soluble anionic polymer is 4 to 9.

6. The method according to claim 1, wherein said water-soluble anionic polymer is added to said aqueous cellulose-derived sugar solution at 0.5 mg/L to 500 mg/L.

7. The method according to claim 1, wherein weight average molecular weight of said water-soluble anionic polymer is 200 to 10000.

8. The method according to claim 1, wherein said fermentation inhibitor(s) is/are one or more of organic acids, furan compounds having a carboxyl group(s), and phenolic compounds having a carboxyl group(s).

9. The method according to claim 8, wherein said fermentation inhibitor(s) comprise(s) acetic acid or formic acid.

10. The method of claim 1, further comprising the step of filtering the sugar liquid through an ultrafiltration membrane having a molecular weight cutoff of 500 to 2000.

11. The method according to claim 2, wherein said water-soluble anionic polymer comprises a polymer selected from the group consisting of a salt of a phosphate polymer, a phosphate polymer, a salt of a polycarboxylate polymer and a polycarboxylate polymer.

12. The method according to claim 2, wherein the pH of said aqueous cellulose-derived sugar solution after addition of said water-soluble anionic polymer is 4 to 9.

13. The method according to claim 3, wherein the pH of said aqueous cellulose-derived sugar solution after addition of said water-soluble anionic polymer is 4 to 9.

14. The method according to claim 4, wherein the pH of said aqueous cellulose-derived sugar solution after addition of said water-soluble anionic polymer is 4 to 9.

15. The method according to claim 2, wherein said water-soluble anionic polymer is added to said aqueous cellulose-derived sugar solution at 0.5 mg/L to 500 mg/L.

16. The method according to claim 3, wherein said water-soluble anionic polymer is added to said aqueous cellulose-derived sugar solution at 0.5 mg/L to 500 mg/L.

17. The method according to claim 4, wherein said water-soluble anionic polymer is added to said aqueous cellulose-derived sugar solution at 0.5 mg/L to 500 mg/L.

18. The method according to claim 5, wherein said water-soluble anionic polymer is added to said aqueous cellulose-derived sugar solution at 0.5 mg/L to 500 mg/L.

19. The method of claim 1, further comprising the steps of:
a) adding the sugar liquid as a feedstock to a fermentor comprising a microorganism;
b) culturing the microorganism to make a chemical product; and
c) isolating the chemical product made in step (b), wherein the sugar liquid is thus used to make a chemical product.

* * * * *